United States Patent [19]

Raikhel

[11] Patent Number: 6,133,507
[45] Date of Patent: Oct. 17, 2000

[54] NETTLE LECTIN CDNA

[75] Inventor: Natasha V. Raikhel, Okemos, Mich.

[73] Assignee: Board of Trustees operating Michigan State University, East Lansing, Mich.

[21] Appl. No.: 07/791,931

[22] Filed: Nov. 12, 1991

[51] Int. Cl.$^7$ .............................. C12N 5/00; C07H 21/04
[52] U.S. Cl. ..................... 800/301; 435/320.1; 536/23.1; 536/23.6
[58] Field of Search .................... 800/205; 435/320.1; 935/11, 14

[56] References Cited

U.S. PATENT DOCUMENTS

| | | | |
|---|---|---|---|
| 4,394,443 | 7/1983 | Weissman et al. | 435/6 |
| 4,940,840 | 7/1990 | Suslow et al. | 800/205 |

OTHER PUBLICATIONS

Aebersold, R.H., et al. PNAS 84 (1987) pp. 6970–6974.
Jaynes, J.M., et al. Trends in Biotech., vol. 4 (1986) pp. 314–320.
Chrispeels, M.J. and Raikhel, N.V., Plant Cell 3:1–9 (1991).
Murdock, L.L. et al., Phytochemistry 29:85–89 (1990), $1^{st}$ page (p. 85) missing.
Czapla, T.H. and Lang, B.A., J. Econ. Entomol. 83:2480–2485 (1991).
Schlumbaum, A., et al., Nature, 324:365–367 (1986).
Van Parijs, J., et al., Planta, 183: 258–264 (1991).
Broekaert, W.F. et al., Science, 245, 1100–1102 (1989).
Huesing, J.E et al., Phytochemistry, in Press (1991).
Peumans, W.J., et al., FEBS Letters 177:99–103 (1984).
Chapot, M P, et al., FEBS Letters 195:231–234 (1986).
Van Damme, E.J.M., and Peumans, W.J., Plant Physiol. 86:598–601 (1988).
Gaynor, J.J., Nucleic Acids Res. 16:5210–5210 (1988).
Shinshi, H., et al., Proc. Natl. Acad. Sci. USA 84: 89–93 (1987).
Broglie, K.E. et al., Proc. Natl. Acad. Sci. USA 83:6820–6824 (1986).
Parsons, T.J. et al., Proc. Natl. Acad. Sci. USA 86:7895–7899 (1989).
Payne, G., et al., Proc. Natl. Acad. Sci. USA 87:98–102 (1990).
Leah, R., et al., JBC 266:1564–1573 (1991).
An, G., et al., Plant Molec. Biol. A3, 1–19 (1988).
Kay, R., et al., Science 236: 1299–1302 (1987).
Horsch, R.B., et al., Plant Mol. Biol., A5 1–9 (1988).
Silflow, C.D., et al., Biochem, 18:2725–2731 (1979).
Nagy, F. et al., Plant Mol. Biol. Manual B4, 1–29 (1988).
Raikhel and Wilkins, P.N.A.S. 84:6745–6749 (1987).
Feinberg and Vogelstein, Anal. Biochem., 132, 6–13 (1983).
Sanger, F., et al., Proc. Natl. Acad. Sci. US 74:5463–5467 (1977).
Lerner and Raikhel, Plant Physiol., 91:124–129 (1989).
Dale, R.M.K., et al., Methods Enzymol. 155:204–214 (1987).
Dellaporta, et al., A Plant Miniprep Version II Plant Mol. Biol. Reporter 1:19–21 (1983).
Wirth & Wolf, Journ. of Microbiological Methods 12 : 197–205 (1990).
Studier, et al., Methods in Enzymology, 185 :60 (1990).
Gait, et al., Nucleic Acids Research Symposium 7:243–257 (1980).
Van Damme, E.J.M. & Peumans, W.J., Physiol. Plantarum 71:328–333 (1987).
Walujono, K., et al., In Proc. Interntl. Rubber Conf. 518–531 (1975).
Broekaert, W.F., et al., Wound–induced accumulation of mRNA containing a heven sequence in Laticifers of rubber tree (Hevea brasiliensis) Proc. Natl. Acad. Sci. US 87:7633–7637 (1990).
Lee, H.I., et al., JBC, 266 (1991) pp. 15944–15948.
Raikhel, N.V., et al., Develop. Genetics, vol. 12 (1991) pp. 255–260.
Beremand, P.D., et al., Archives of Biochem. & Biophysics, 256:90–100 (1987).

*Primary Examiner*—Bruce R. Campbell
*Attorney, Agent, or Firm*—Ian C. McLeod

[57] ABSTRACT

A cDNA encoding a chitin-binding protein of nettle lectin (*Urtica dioica*) and subunits thereof is described. The cDNA is incorporated into a vector so as to be transformed into a plant. A synthetic gene encoding a chitin binding protein is also described.

22 Claims, 11 Drawing Sheets

Nettle lectin cDNA clone

```
        AATCATAGTA AGAAAGAAAA G ATG ATG ATG AGG TTT TTA TCT GCC GTA   48
                               Met Met Met Arg Phe Leu Ser Ala Val
                                           -20                  -15

GTG ATC ATG TCC TCC GCT ATG GCG GTG GGT CTA GTG TCG GCA CAG AGG    96
Val Ile Met Ser Ser Ala Met Ala Val Gly Leu Val Ser Ala Gln Arg
            -10                  -5                           1

TGC GGA AGC CAA GGC GGC GGG GGT ACG TGT CCC GCC TTG TGG TGC TGC   144
Cys Gly Ser Gln Gly Gly Gly Gly Thr Cys Pro Ala Leu Trp Cys Cys
         5                   10                      15

AGC ATC TGG GGC TGG TGC GGC GAC TCG GAG CCC TAC TGC GGC CGC ACC   192
Ser Ile Trp Gly Trp Cys Gly Asp Ser Glu Pro Tyr Cys Gly Arg Thr
        20                  25                  30

TGC GAG AAC AAG TGC TGG AGC GGC GAG CGG TCG GAC CAC CGC TGC GGC   240
Cys Glu Asn Lys Cys Trp Ser Gly Glu Arg Ser Asp His Arg Cys Gly
35                  40                  45                  50

GCC GCT GTA GGA AAC CCT CCG TGC GGC CAG GAC CGG TGC TGC AGC GTC   288
Ala Ala Val Gly Asn Pro Pro Cys Gly Gln Asp Arg Cys Cys Ser Val
                55                  60                  65

CAC GGG TGG TGC GGT GGC GGC AAC GAC TAC TGC TCC GGG AGC AAA TGC   336
His Gly Trp Cys Gly Gly Gly Asn Asp Tyr Cys Ser Gly Ser Lys Cys
            70                  75                  80

CAG TAC CGC TGC TCC TCC TCC GTC CGT GGA CCC CGC GTC GCT CTC AGC   384
Gln Tyr Arg Cys Ser Ser Ser Val Arg Gly Pro Arg Val Ala Leu Ser
        85                  90                  95

GGC AAT TCC ACC GCC AAC TCC ATC GGC AAC GTC GTC GTC ACC GAG CCG   432
Gly Asn Ser Thr Ala Asn Ser Ile Gly Asn Val Val Val Thr Glu Pro
    100                 105                 110

CTG TTC GAC CAG ATG TTC TCC CAC CGC AAG GAC TGT CCG AGC CAG GGC   480
Leu Phe Asp Gln Met Phe Ser His Arg Lys Asp Cys Pro Ser Gln Gly
115                 120                 125                 130

TTC TAC AGC TAC CAC TCC TTC CTC GTA GCC GCC GAG TCC TTC CCA GCT   528
Phe Tyr Ser Tyr His Ser Phe Leu Val Ala Ala Glu Ser Phe Pro Ala
                135                 140                 145

TTC CTC GCC CAT ATC TCC CAA GCA ACA TCA GGG GAA AGG TCT GAC GTG   576
Phe Gly Thr Ile Gly Asp Val Ala Thr Arg Lys Arg Glu Val Ala Ala
            150                 150                 160
```

FIG. 2b-1

```
TTC GGG ACC ATC GGA GAT GTT GCG ACA CGC AAG AGA GAG GTC GCA GCG   624
Phe Leu Ala His Ile Ser Gln Ala Thr Ser Gly Glu Arg Ser Asp Val
        165             170             175

GAA AAC CCT CAT GCA TGG GGG CTT TGT CAT ATC AAT ACA ACT ACT GTG   672
Glu Asn Pro His Ala Trp Gly Leu Cys His Ile Asn Thr Thr Thr Val
        180             185             190

ACT GAG AAT GAC TTC TGT ACC TCC TCC GAC TGG CCT TGC GCT GCC GGC   720
Thr Glu Asn Asp Phe Cys Thr Ser Ser Asp Trp Pro Cys Ala Ala Gly
195             200             205             210

AAA AAA TAC AGC CCT CGA GGA CCC ATC CAG CTC ACC CAC AAC TTC AAC   768
Lys Lys Tyr Ser Pro Arg Gly Pro Ile Gln Leu Thr His Asn Phe Asn
        215             220             225

TAC GGA CTT GCC GGC CAA GCC ATT GGA GAG GAC CTG ATT CAG AAC CCT   816
Tyr Gly Leu Ala Gly Gln Ala Ile Gly Glu Asp Leu Ile Gln Asn Pro
        230             235             240

GAC TTG GTA GAA AAG GAT CCA ATC ATA TCA TTC AAG ACG GCC TTG TGG   864
Asp Leu Val Glu Lys Asp Pro Ile Ile Ser Phe Lys Thr Ala Leu Trp
        245             250             255

TTC TGG ATG TCC CAG CAC GAC AAC AAA CCT TCA TGC CAT GAC ATT GTC   912
Phe Trp Met Ser Gln His Asp Asn Lys Pro Ser Cys His Asp Ile Val
        260             265             270

CTC AAT GCC AAC TCC GCC GCG AAC AGA ATC CCA AAC AAA GGT GTG ATC   960
Leu Asn Ala Asn Ser Ala Ala Asn Arg Ile Pro Asn Lys Gly Val Ile
275             280             285             290

GGC AAC ATT ATT AGC CGC GCT TTT GGG CAC GAC GAC TTT GCC GTT AGA   1008
Gly Asn Ile Ile Ser Arg Ala Phe Gly His Asp Asp Phe Ala Val Arg
        295             300             305

TCT TCA AGC ATC GGA TTT TAC AAG AGG TAC TGC GAC ATG CTG GGA GTG   1056
Ser Ser Ser Ile Gly Phe Tyr Lys Arg Tyr Cys Asp Met Leu Gly Val
        400             405             410

AGC TAT GGA CAT GAC TTG AAG TAC TGG TTC GAT AAC ACT CCA TCA TCG   1104
Ser Tyr Gly His Asp Leu Lys Tyr Trp Phe Asp Asn Thr Pro Ser Ser
        415             420             425

GAG TTC CAA CGC ATC CAA ATG CGT GTT GCG GCG TAAAACAAGC TAGTCCTCCC  1158
Glu Phe Gln Arg Ile Gln Met Arg Val Ala Ala
        430             435

CAAGTGGCTC TCTAGTAGTA AGAGTAGCTC TCTCATAGCG AGAGAGCGGC ATGTTGAATC  1218

CCTGTTATGC TATGTAATAT TATGTTACGC ATGTATGTTA GAAACATATA TGTGTGATTT  1278

TCTAGCTCTT ACGAGTTATA AATAAAGTAG CCACTTTCCT                        1317
```

FIG. 2b-2

COMPARISON OF UDA AMINO ACID SEQUENCES

UDA cDNA1:
(deduced)   QR/ CGSQGGGGTCPALWCCSIWGWCGDSEPYCGR/ TCENK/ CWSGER/ SDHR/ CGAAVGNPPCGQDR/ CCSVHGWCGGGNDYCSGSK/ CQYR/ C UDA tryptic
fragments:  QR/ CGS

FIG. 6

NETTLE LECTIN CDNA

BACKGROUND OF THE INVENTION

(1) Field of the Invention

The present invention relates to cDNA encoding a chitin binding protein (lectin) of rhizomes of Urtica dioica (nettle lectin). The chitin binding protein (lectin) is provided in a vector for transforming plants to impart insecticidal activity to cells of the plant, particularly in the leaves of the plant.

(2) Prior Art

Chitin-binding proteins have been found in a wide range of species, including both monocots and dicots, even though plants contain no chitin. These proteins are related by the presence of a conserved 43 amino acid cysteine and glycine rich domain. In some of these proteins the chitin-binding domain has been duplicated and appears in tandem repeats. In others, this domain has been fused to an unrelated domain. In vitro experiments using many different chitin-binding proteins suggest they may be involved in plant defense against insects or fungal pathogens.

Chitin, a polymer of β-1,3-N-acetyl-glucosamine, is found in the cell wall of many fungi, the exoskeleton and digestive tract of some insects and in some nematodes. It is curious then that plants, which contain no chitin, express a family of chitin-binding proteins with a conserved chitin-binding domain. These plants range from wheat to rubber trees and stinging nettle. Chitin-binding proteins are secretory proteins which may be involved in plant defense (Chrispeels, M. J. and Raikhel, N. V., Plant Cell 3:1–9 (1991)). Several genes and proteins from this family have been isolated and characterized. Some of them, for example the Gramineae lectins, have been shown to have insecticidal activity by in vitro experiments (Murdock, L. L., et al., Phytochemistry 29:85–89 (1990); Czapla, T. H. and Lang, B. A., J. Econ. Entomol. 83:2480–2485 (1991)). Others, such as the basic chitinases and hevein, possess antifungal activity in in vitro experiments (Schlumbaum, A., et al., Nature, 324:365–367 (1968); Van Parijs, J., et al., Planta, 183, 258–264 (1991)). Recently, a chitin-binding protein isolated from the rhizomes of stinging nettle (Urtica dioica) (Urtica dioica), Urtica dioica agglutinin (UDA), has been shown to possess both antifungal and insecticidal activities (Broekaert, W. F., et al., Science, 245, 1100–1102 (1989); Huesing, J. E., et al., Phytochemistry, in press (1991)).

The rhizomes of stinging nettle serve as underground storage tissues and as a source of vegetative meristems for regeneration of shoots in the spring. For both these functions rhizomes would require mechanisms for protection against soil pathogens. UDA has been found to accumulate to high levels (1 gm/kg) in the rhizomes (Peumans, W. J., et al., FEBS Letters 177:99–103 (1983)). This small protein, 8.5 kDa, is rich in glycine and cysteine residues and has been shown to have homology to other chitin-binding proteins (Chapot, M-P, et al., FEBS Letters 195:231–234 (1986)). Several isoforms, isolectins, of UDA have been isolated (Van Damme, E. J. M., and Peumans, W. J., Plant Physiol. 86:598–601 (1988)).

OBJECTS

It is an object of the present invention to provide cDNA nettle lectin which has insecticidal properties. Further, it is an object of the present invention to provide vectors and transformed plants incorporating the cDNA. These and other objects will become increasingly apparent by reference to the following description and the drawings.

IN THE DRAWINGS

FIG. 1 is a schematic diagram of the sequential ligation reactions used to produce the synthetic UDA gene (SEQ ID NO:2) from the 18 synthetic oligonucleotides. Complimentary pairs of purified phosphorylated oligonucleotides (i.e. #1+#2, #3+#4, etc.) were annealed in separate reactions. Annealed pairs of oligonucleotides were sequentially ligated from the ends of the synthetic gene as shown. The full length synthetic gene was restricted at EcoRI sites positioned near the ends of the gene and ligated into pUC119 for sequence analysis.

FIG. 2a is a diagram of the UDA cDNA clone uda1 showing the domain structure of the encoded polypeptide. The putative signal sequence, N-terminal domain encoding UDA, linker/spacer, and C-terminal domain are shown.

FIG. 2b is a DNA sequence of the UDA cDNA clone uda1 (SEQ ID NO:1). The translation initiation codons at the start of the open reading frame and potential polyadenylation signal are underlined. Deduced amino acids are listed below the nucleotide sequence and numbered respective the start of mature UDA.

FIG. 3 is a Northern blot analysis of Urtica dioica rhizome total RNA, 20 ug per lane. Lanes 1 and 2 were probed with $^{32}P$ labeled DNA corresponding to the N-terminal and C-terminal domains respectively. RNA size markers in kilobases are shown to the left of the autoradiogram.

FIG. 4 is a PCR analysis using reverse transcribed total RNA from Urtica dioica as the template with primers from uda1. A) Diagram showing positions of the primers on the cDNA clone. B) PCR products were separated by electrophoresis on a 1% agarose gel containing 0.5 ug/ml ethidium bromide and visualized with UV light. Lanes 2, 3, and 4 are total PCR products generated with the primers indicated. HindIII cut lambda DNA with AluI cut pBR322 are the size standards (lane 1).

FIG. 5 is a comparison of UDA amino acid sequences. Alignment of amino acid sequence from Edman degradation of UDA tryptic digests (Chapot, M-P, et al., FEBS Letters 195:231–234 (1986)) with the deduced amino acid sequence of uda1 (SEQ ID NO:4). Trypsin cleavage sites are indicated with a slash (/). Non-identical amino acids are underlined. Incompletely sequenced tryptic fragments are indicated with a dash (-).

FIG. 6 is a comparison of uda1 deduced amino acid sequence (SEQ ID NO:4) with the deduced amino acid sequences of various chitinases. Putative signal sequences, chitin-binding domains, hinge regions and chitinase catalytic domains are indicated. Sequences were aligned manually with gaps to preserve the highest degree of similarity. Amino acids identical to uda1 are denoted with a vertical line (|), conservative amino acid substitutions are denoted with a colon (:) and gaps in the aligned sequences are denoted with a dash (-). Amino acid sequences were derived from nucleotide sequence in the GenBank database [accession numbers: Potato chitinase (SEQ ID NO:5), X08011 (Gaynor, 1988); Tobacco chitinase I (SEQ ID NO:6), M15173 (Shinshi, H, et al., Proc. Natl. Acad. Sci. U.S.A. 84:89–93 (1987)); Bean chitinase (SEQ ID NO:7), M13968 (Broglie, K. E., et al., Proc. Natl. Acad. Sci. U.S.A. 83:6820–6824 (1986)); Poplar chitinase (SEQ ID NO:8), M25337 (Parsons, T. J., et al., Proc. Natl. Acad. Sci. U.S.A. 86:7895–7899 (1989)); Tobacco chitinase II (SEQ ID NO:9), M29869 (Payne, G., et al., Proc. Natl. Acad. Sci. U.S.A. 87:98–102 (1990)); Barley chitinase (SEQ ID NO:10), M36989 (Leah, R., et al., JBC 266:1564–1573 (1991))].

FIG. 7 is a Southern blot analysis of *Urtica dioica* genomic DNA. 40 ug genomic DNA was digested two times 20 hours with 16 U BamHI (lane 1), 80 U BamHI (lane 2), 160 U BamHI (lane 3), 160 U HindIII (lane 4) or 160 U XbaI (lane 5). 5 ug digested DNA (lanes 1–5) or undigested DNA (lane 6) was loaded per lane on a 0.8% agarose gel, blotted to nitrocellulose and probed with $^{32}P$ labeled uda1 washed at high stringency (0.2× SSC+0.1% SDS at 65° C.) and visualized with autoradiography.

GENERAL DESCRIPTION

Figure 1:
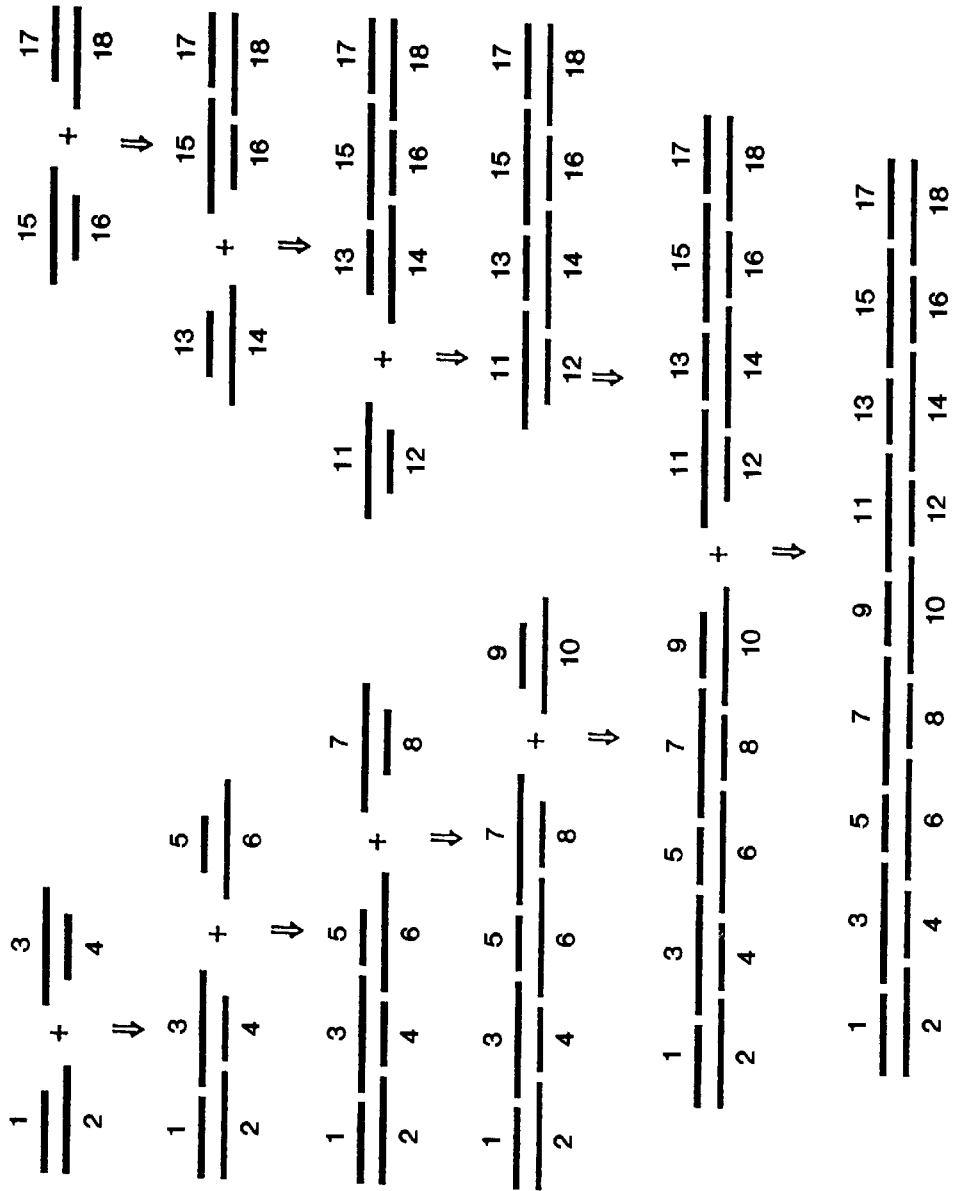

The present invention relates to a cDNA encoding a chitin binding protein of rhizomes of *Urtica dioica* and subunits of the cDNA which encode a peptide which is chitin binding. Further, the present invention relates to a vector DNA for transferring DNA between unrelated organisms fused to a cDNA encoding a chitin binding peptide of rhizomes of *Urtica dioica* and subunits of the cDNA which is chitin binding. Also the present invention relates to a transgenic plant containing cDNA encoding a chitin binding peptide of rhizomes of *Urtica dioica* and subunits of the cDNA which is chitin binding fused to a promoter DNA which produces expression of the protein in the plant. A promoter useful for expression of the present invention in plants is the tandem duplicated cauliflower mosaic virus 35S promoter. Finally the synthetic gene (SEQ ID NO:2) and its encoded amino acid sequence (SEQ ID NO:3) is as follows:

```
CAG AGG TGC GGA TCT CAA GGA GGT GGC GGA ACT TGC CCT GCT CTT AGG      48
Gln Arg Cys Gly Ser Gln Gly Gly Gly Gly Thr Cys Pro Ala Leu Arg
 1           5                  10                  15

TGT TGC AGC ATT TGG GGA TGG TGT GGA GCT AGC AGC CCA TAT TGT GGC      96
Cys Cys Ser Ile Trp Gly Trp Cys Gly Ala Ser Ser Pro Tyr Cys Gly
            20                  25                  30

AAG GGA TGC CAG TAC AGA TGC TGG AGC GGA GAA AGA TGC GGA GCT CAA     144
Lys Gly Cys Gln Tyr Arg Cys Trp Ser Gly Glu Arg Cys Gly Ala Gln
        35                  40                  45

GTT GGA AAC CCA ACT TGC GGA CAA CTT AGG TGT TGC AGC GTT CAT GGG     192
Val Gly Asn Pro Thr Cys Gly Gln Leu Arg Cys Cys Ser Val His Gly
    50                  55                  60

TGG TGT GGA GGA GGT AAT GAC TAT TGT                                 219
Trp Cys Gly Gly Gly Asn Asp Tyr Cys
```

To investigate the relationship between in vitro activities and endogenous functions of chitin binding proteins, a stinging nettle lectin (*Urtica dioica* agglutinin, UDA) cDNA was cloned using a synthetic gene as the probe. The UDA cDNA contains an open reading frame encoding 263 amino acids beyond the UDA encoding sequence (SEQ ID NO:1). The veracity of the clone was confirmed by deduced amino acid sequence identity with sequence data from tryptic digests, Northern blot analysis and PCR. The deduced amino acid sequence contains the two 43 amino acid chitin-binding domains of UDA fused to a domain similar to a chitinase catalytic domain. This is the first example of a chitin binding protein with both a domain duplication and domain fusion. In addition, RNA gel blot analysis showed UDA message was present primarily in the flower pods (with seeds) and rhizomes but not in leaves, stems, or male flowers. The message was (not) also shown to be induced in the leaves by wounding. Bacterial expression of the cDNA encoding domains, alone or linked together, demonstrated [chitin binding and chitinase activities].

The isolation of a cDNA clone encoding UDA was accomplished using a synthetic UDA gene (SEQ ID NO:2) as the probe. The cDNA clone was found to encode UDA at the amino-terminal portion of the deduced polypeptide along with an unexpected carboxyl-terminal domain. Validity of the clone was addressed by several approaches and the predicted properties of both domains were analyzed by expression in *E. coli.*

The present invention also involves the use of a vector for the transformation of plants which encode the UDA cDNA of the present invention. A promoter useful for expression of the present invention in plants is the tandem duplicated cauliflower mosaic virus 35S promoter. In this manner the transformed plants encode a chitin binding protein which the insects ingest and which ultimately inhibit or kill the insect. The insects are those that are affected by the chitin binding protein. Suitable vectors are for instance pGA643, An, G. et al., Plant Molec. Biol., A3, 1–19 (1988); PMAT 137, Kay, R. et al., Science 236:1299–1302 (1987). Other methods for introducing the cDNA into the plant are agrobacteria-medicated transformation was accomplished via the leaf disc method of Horsch, R. B., et al., Plant Mol. Biol., A5, 1–9 (1988). The methods used are well known to those skilled in the art.

SPECIFIC DESCRIPTION MATERIALS AND METHODS

Plant Material

Plant material was grown under standard greenhouse conditions. *Urtica dioica* seed was from Dr. W. J. Peumans (Katholieke Univ. Leuven, Belgium) or ([Egessa, Germany)]. Rhizomes were generated by burying cut stems under 1 to 2 cm soil and grown in the greenhouse. These rhizomes were tested for the presence of UDA by agglutination of trypsin-treated rabbit erythrocytes (Van Damme, E. J. M., Plant Physiol., 86:598–601 (1988)).

RNA Isolations

Rhizomes were washed free of soil, blotted dry, frozen in liquid $N_2$ and stored at −80° C. Frozen tissue was ground in liquid $N_2$ then mixed with 2.6 ml/gm extraction buffer (0.2 M Tris-HCl pH 9.0, 0.4 M NaCl, 0.025 M EGTA, 1% SDS, 0.5% PVP-40) and ground further with a polytron for 4 minutes. Proteinase K (0.5 mg/ml) was added and incubated at 37° C. with constant mixing for 60 minutes. The extract was then mixed with BaCl (0.075 M) and KCl (0.035 M), incubated on ice 15 minutes, centrifuged at 10 krpm for 10 minutes at 4° C. and the supernatant filtered through Miracloth (Calbiochem, San Diego, Calif.). RNA in the supernatant was precipitated with LiCl (2 M) at −20° C. overnight and collected by centrifugation at 7 krpm for 20 minutes at 4° C. The pellet was resuspended in TE (10 mM Tris-HCl pH 8, 0.1 mM EDTA) and the RNA reprecipitated with sodium acetate and ethanol (Maniatis, T., et al., Molecular Cloning: A Laboratory Manual. Cold Spring Harbor Laboratory. Cold Spring Harbor, N.Y. (1982)) and stored at −20° C. Poly(A)+RNA was isolated from total RNA with oligo-dT sepharose (Silflow, C. D., et al., Biochem, 18:2725–2731 (1979)). Total RNA from all other tissues was isolated by the method of Nagy et al (Nagy, F., et al., Plant Mol. Biol. Manual B4, 1–29 (1988)).

RNA Gel Blot Analysis

RNA gel blot analysis was performed by separating 20 ug total RNA per lane and 5 ul RNA ladder (BRL, Gaithersburg, Md.) as size standards on 1 2% agarose/formaldehyde gel as previously described (Raikhel and Wilkins, P.N.A.S. 84:6745–49 (1987)). Medium stringency washes were done with 2x SSC with 0.1% SDS at 65° C. High stringency washes were done with 0.2xSSC with 0.1% SDS at 65° C. $^{32}$P-labelled probes were prepared with random primers (Feinberg and Vogelstein, Anal. Biochem., 132, 6–13 (1983)), the unincorporated nucleotides were removed with Nuctrap columns (Stratagene, San Diego Calif.).

Oligonucleotide Synthesis and Purification

Oligonucleotides were synthesized using β-cyanoethyl chemistry on an Applied Biosystems DNA synthesizer (Model 380B, Foster City, Calif.) by the Macromolecular Structure Facility (Michigan State Univ., East Lansing, Mich.). Purification of the oligonucleotides was by gel electrophoresis (Sambrook, T. et al., Molecular Cloning: A Laboratory Manual, 2nd ed. (Cold Spring Harbor, N.Y. (1990)) or HPLC using a Zorbax Bioseries oligo column (Dupont). Purified oligonucleotides were desalted with SEP-PAK C-18 columns (Waters Associates, Bedford, Mass.) as recommended by the manufacturer.

Synthetic Gene Assembly

One nmol of each purified oligonucleotide, except those at the terminal 5' ends of the synthetic gene, were phosphorylated with $T_4$ polynucleotide kinase (New England Biolabs) (Sambrook, T., et al Molecular Cloning: A Laboratory Manual, 2nd ed. (Cold Spring Harbor, N.Y. (1990)) and separated from free nucleotides with Nuctrap push columns (Stratagene, LaJolla, Calif.), 10 mM Tris was used instead of the recommended buffer (20 mM Tris, 100 mM NaCl, 10 mM EDTA).

Complementary pairs of oligonucleotides, 200 pmol each, were annealed by heating to 80° C. then cooling slowly to room temperature. The annealed pairs, 100 pmol each, were then ligated in sequential reactions. Initially, the outermost pairs of annealed oligonucleotides were mixed with the adjacent pair in separate reactions which included 60 units $T_4$ DNA ligase (New England Biolabs, Beverly, Mass.), 200 mM Tris-HCl (pH 7.6), 50 mM $MgCl_2$, 50 mM dithiothreitol (DTT) and 500 ug/ml bovine serum albumin (BSA) and then incubated for 30 minutes at 15° C. For subsequent ligation reactions the next adjacent pair of annealed oligonucleotides were added to the previous reaction mix along with 30 units $T_4$ DNA ligase. Tris, $MgCl_2$, DTT, and BSA were also added to bring concentrations to initial values and the reactions incubated for 30 minutes at 15° C. Finally, the two halves were mixed with the addition of 60 units $T_4$ DNA ligase and incubated for 2.5 hours at 15° C. The ligation reactions were stopped by heating to 70° C. and the products precipitated with sodium acetate and ethanol. The synthetic gene was phosphorylated as described above for ligation to the cloning vector, pUC119. At the end of each ligation step, 10% of the reaction mix was removed and assayed for completeness of ligation. Each sample was end labeled with γ-$^{32}$P-ATP, resolved on a 12.5% non-denaturing polyacrylamide gel, and visualized with autoradiography (data not shown).

Cloning the Synthetic UDA Gene

Restriction digests of the synthetic gene and pUC119 vector were performed using Boehringer Mannheim enzymes following the manufacturers instructions. Vector dephosphorylation reactions were performed with calf intestinal phosphatase (Sigma, St. Louis, Mo.) for 30 minutes at 55° C. The synthetic UDA gene (2.5 pmol) and vector (0.25 pmol) were ligated as above with 100 units ligase for 12 hours at 15° C. The ligation products were cloned by standard methods and the sequence of the synthetic gene confirmed with DNA sequencing by the dideoxy chain termination method (Sanger, F., et al., Proc. Natl. Acad. Sci. U.S. 74:5463–5467 (1977)).

Complimentary DNA (cDNA) Library Construction

The lambda gt10 cDNA library was constructed with *Urtica dioica* rhizome poly(A)+RNA and EcoRI adapters (Promega, Madison Wis.) as previously described (Lerner and Raikhel, Plant Physiol., 91:124–129 (1989)). 5×10$^5$ plaque forming units (pfu) of the amplified library (1.5×10$^5$ original pfu) were screened at medium stringency (see above) with random primer labelled synthetic UDA gene. Positive plaques were purified to homogeneity and the cloned DNA isolated. Due to loss of the EcoRI adapter sites during construction of the library insert DNA was isolated by PCR with primers just flanking the EcoRI site of lambda gt10 (5'-AGCAAGTTCAGCCTGGTTAA-3' (SEQ ID NO:11) and 5'-TTATGAGTTATTTCTTCCAGG-3') (SEQ ID NO:12). PCR products were phosphorylated with T4 polynucleotide kinase and ligated into the SmaI site of pUC119 for cloning and sequence analysis. The complete sequence of cDNA clones was obtained with dideoxy chain termination sequencing of deletions generated by the method of Dale and Arrow (Dale, R. M. K., et al., Methods Enzymol. 155:204–214 (1987)).

Polymerase Chain Reaction DNA Amplification

Reactions were carried out with deoxynucleotides, buffers and enzyme concentrations as recommended by the enzyme manufacturer. Taq polymerase (Amplitaq, Perkin Elmer/Cetus, Norwalk, Conn.) was used for amplifying inserts from lambda gt10 library. Replinase (NEN/Dupont, Wilmington, Del.) was used for amplification of reverse transcribed RNA (see below). Reactions were carried out on a Perkin-Elmer thermocycler with an initial denaturation step of 94° C. for 4 minutes; 30 cycles of 94° C. for 1 minute, 65° C. for 2 minutes, 72° C. for 3 minutes; and 72° C. for 7 minutes as a final polymerization step. Reaction products were purified from unincorporated nucleotides with PCR purification columns (Qiagen, Studio City, Calif.). For subcloning, the reaction products were size fractionated on 1% low melting point agarose gels (SeaKem LE, FMC, Rockland, Ma.).

Reverse Transcription with PCR

First strand cDNA was generated from *Urtica dioica* total rhizome RNA using oligo-dT primers and the cDNA synthesis kit from BRL (Gaithersburg, Md.) following the manufacturers instructions with a 20 ul reaction. First strand cDNA was then used as template for the PCR, 5 ul reverse transcription reaction per 25 ul PCR reaction. Primers for the PCR were identical or complimentary to the UDA cDNA clone as specified: #1: 5'-TCTGCCGTAGTGATCATG-3' (nt# 40 to 57) (SEQ ID NO:13), #2:

5'-AGCGGTACTGGCATTTGC-3' (nt #348 to 329) (SEQ ID NO:14), #3: 5'-ATGGTAGCTGTAGAAGC-3' (nt #495 to 479) (SEQ ID NO:15), #4: 5'-GTCGCA GTACCTCTTGTA-3' (nt #1044 to 1027) (SEQ ID NO:16)

Southern Blot Analysis

Genomic DNA was isolated by the method of Dellaporta, et al (Dellaporta, et al., A plant DNA miniprep: version II. Plant Mol. Biol. Reporter 1:19–21 (1983)) and 40 ug were cleaved with BamHI (16, 80 or 160 units), HindIII (160 units), or XbaI (160 units) using standard reaction conditions for 20 hours. The reaction products were extracted with phenol, phenol/$CHCl_3$/Isoamyl alcohol (25:24:1), $CHCl_3$/isoamyl alcohol (24:1), precipitated with sodium acetate and ethanol (Sambrook, T., et al., Molecular Cloning, A Laboratory Manual, 2nd ed. (Cold Spring Harbor, N.Y. (1990)) and resuspended in 10 mM Tris-HCl with 0.1 mM EDTA. This digested DNA was redigested, extracted and precipitated as above then size separated on a 0.8% agarose gel and capillary blotted onto transfer membrane (MSI, Nitroplus). $^{32}$P-labeled uda1 was prepared and used to probe the blot as described for RNA gel blots. Blots were washed at high stringency (0.2x SSC+0.1% SDS) and exposed to autoradiographic film for visualization of bound probe.

Sequence Analysis and Comparisons

Sequence analysis and comparisons were performed with MICROGENIE software (Beckman, Fullerton, Calif.) and EDITBASE software (courtesy of N. Nielsen, Purdue University, West Lafayette, Ind.). Amino acid sequence of the chitinase genes was deduced from the nucleotide sequence in Genebank. Amino acid sequence alignments were done manually. ps Expression of the uda1 Encoded Domains in *E. coli*.

Oligonucleotide directed mutagenesis (Dale, R. M. K. and A. Arrow, Methods Enzymol. 155:204–214 (1987)) was used to insert restriction sites into the cDNA for convenient cloning into the T7 RNA polymerase *E. coli* expression vector pET3a (Studier, et al., Methods in Enzymology, 185:60 (1990)). One oligonucleotide (#1: 5'-GGT CTAGTGTCGGCATATGCAGAGGTGCGGAAGC-3') (SEQ ID NO:17) was used to insert an NdeI site at the beginning of the region encoding the mature UDA. A second oligonucleotide (#2: 5'-GCCAGTACCGCTGC TAACATATGATCGGCAACGTCGTCG-3') (SEQ ID NO:18) was used to insert a stop codon immediately following the sequence encoding mature UDA along with an NdeI site at the beginning of the chitinase-like region. A third oligonucleotide (#3: 5'-TGTTGCGGC GTAAAACATATGCTAGTCCTCCCCAAG-3') (SEQ ID NO:19) was used to place an NdeI site just following the stop codon for the open reading frame. Pairs of these oligonucleotides were then used in separate mutagenesis reactions to contract NdeI bound inserts encoding the mature UDA (#1 and #2), the chitinase-like region (#2 and #3), and the entire open reading frame without the putative signal sequence (#1 and #3). Mutagenized nettle lectin cDNAs were sequenced to confirm mutagenesis and check for errors introduced during mutagenesis. These inserts were ligated into the NdeI site of pET3a for expression of the polypeptides in *E. coli*. *E. coli*, BL21(DE3) (Studier, et al., Methods in Enzymology, 185:60 (1990)), cultures containing the constructs were grown to $OD_{595}$ 0.5, induced with 100 uM IPTG and incubated for 5 hours. Cells were collected by centrifugation and resuspended in 1 ml/gm extraction buffer (50 mM Tris (pH 8.0), 1 mM EDTA, and 100 mM NaCl). Crude lysate was prepared by freezing the cell suspension at −20° C., thawing at 37° C. for 20 minutes, and removing the cell debri by centrifugation at 15 kRPM for 15 minutes.

Chitinase Assay

The colorimetric chitinase assay was performed by the method of Wirth and Wolf (Wirth and Wolf, Journ. of Microbiological Methods, 12:197–205 (1990)). Briefly, two parts crude extract, diluted to 1 ug/ul protein with extraction buffer, was mixed with one part 0.2 M sodium acetate (pH 3.6) and one part chitin dye substrate (carboxymethyl-chitin-Remazol Brilliant Violet 5R (CM-chitin-RBV) and then incubated at RT for 12 hours. Undegraded substrate was precipitated with one part 1 M HCl for 10 minutes on ice and removed by centrifugation 3.5 kRPM 10 minutes. Absorbance at 550 nm was used to measure soluble RBV released by the chitinase activity in the extracts. A blank was prepared with extraction buffer in place of the *E. coli* extract.

Results

The gene for UDA was cloned. Initial attempts to use the gene for another chitin-binding protein (Barley lectin) as a heterologous probe were unsuccessful due to insufficient specificity as determined by RNA gel blot analysis (data not shown). After unsuccessful attempts to generate a specific probe by PCT, it was decided to synthesize a gene for UDA.

Design of the Gene for UDA

The amino acid sequence of UDA as determined by Chapot et al., FEBS Lett., 195:231–234 (1985)) and Steve Michnick (personal communication) was used as a template for designing the synthetic gene. Since the synthetic gene was intended for expression in transgenic tomato, codon usage was primarily a consensus of tomato genes (Genbank, version 59, 3/89). In addition, several highly conserved amino acid residues among the chitin-binding proteins showed similar codon usage. In these cases, the conserved codon superseded the tomato codon usage. Codon usage was further modified to prevent long stretches of guanidine residues which are difficult to synthesize accurately (Gait, et al, Nucleic Acids Research Symposium 7:243–257 (1980)). Where four guanidine residues in a row were unavoidable, such as tryptophan (TGG) next to Glycine (GGX), the guanidine residues were split between two adjacent oligonucleotides. Complementary pairs of oligonucleotides were designed to contain one 5' and one 3' eight base overhang. This greatly reduced the potential for mispaired ligations compared to pairs with two 5' or 3' overhangs. Restriction endonuclease recognition sites were included in the synthetic gene flanking the coding region for UDA to facilitate cloning. In addition, three extraneous base pairs were added to each end of the synthetic gene since exonuclease activity during construction can obliterate restriction sites at the extreme ends of the gene.

Assembly and Cloning of the Synthetic Gene

Sequential ligation reactions of annealed pairs were done in two separate reactions starting at each end of the gene, the two half-genes were then ligated together (FIG. 1). This strategy was used to limit the number of potential mismatched ligations. Each ligation step was assayed by end-labeling the reaction products with $^{32}$P, separating them by denaturing polyacrylamide gel electrophoresis and visualization by autoradiography (data not shown). These data indicated that both complete and partial ligation products were present at each step. The final ligation reaction products were phosphorylated at the 5' end or restricted with SmaI or EcoRI and ligated into appropriately restricted and dephosphorylated pUC119. Only vector ligations with EcoRI restricted synthetic gene successfully transformed *E. coli*. Sequence analysis showed that several synthetic gene clones were missing single base pairs but most were accurately synthesized and assembled. One of the accurately synthesized clones was used for further experiments.

Isolation of a cDNA Clone for UDA

Figure 2A:
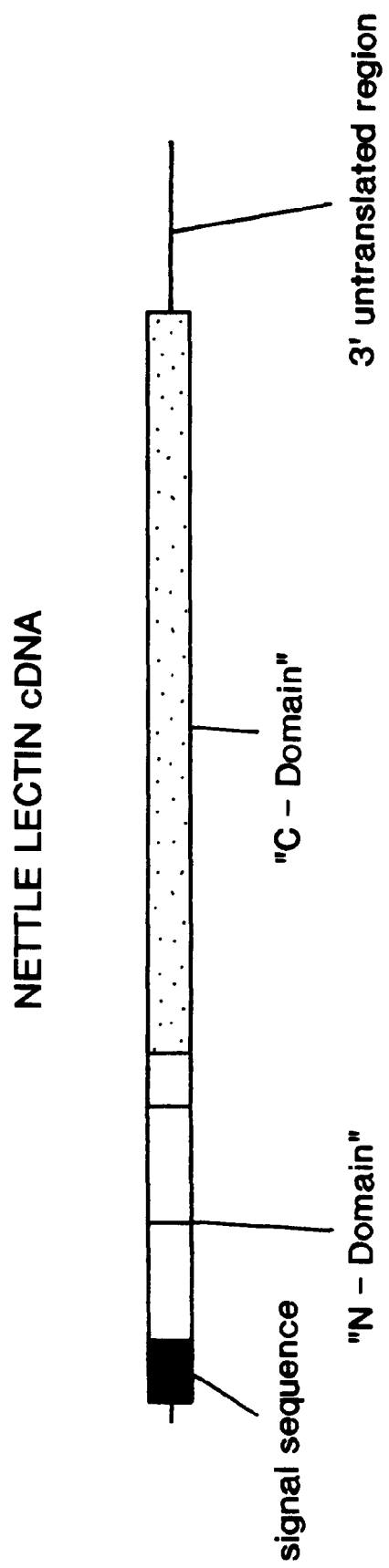

The synthetic gene was used as the probe to screen an amplified stinging nettle rhizome cDNA library. Eight positive plaques were purified through successive rounds of screening and their inserts isolated via PCR due to loss of the EcoRI restriction sites during library construction. Isolated inserts were subcloned into pUC119 and analyzed by dideoxy chain termination sequencing. One clone, uda1, contained sequence encoding UDA and was completely sequenced in both directions. Uda1 was approximately 72% identical to the synthetic gene used as the probe. Although the deduced amino acid sequence for UDA was only 86 amino acids long, uda1 encoded an open reading frame of 372 amino acids (FIG. 2). The deduced amino acid sequence included a putative signal peptide (23 amino acids), the UDA domain (86 amino acids), a 'spacer' domain (19 amino acids), and a 244 amino acid carboxyl-terminal domain.

Determining the Veracity of the cDNA Clone

Figure 3:
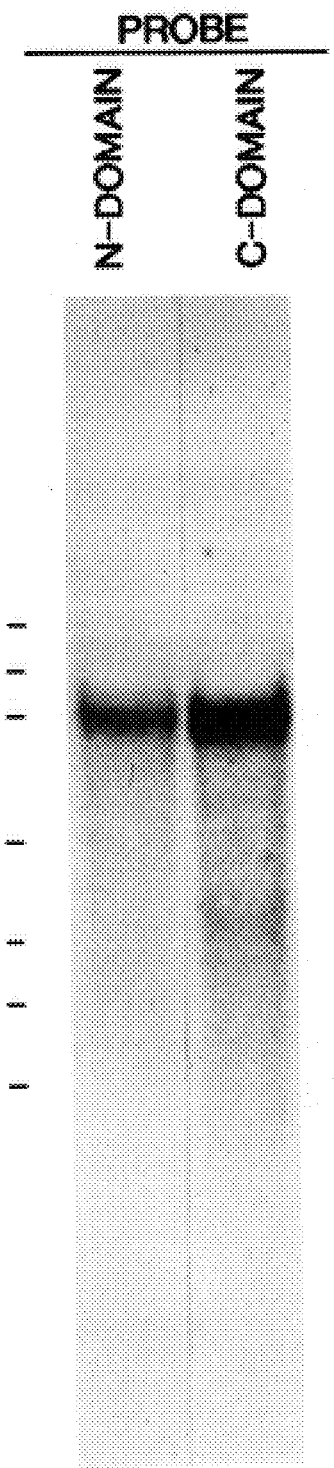

The unexpected structure of uda1 prompted the use of several methods to verify that the isolated cDNA corresponded to the actual message for UDA. First, RNA gel blot analysis of stinging nettle rhizome total RNA was performed to analyze the hybridization pattern with clone fragments corresponding to the UDA encoding domain (FIG. 3, lane 1) or the carboxyl-terminal domain (FIG. 3, lane 2). A single band of approximately 1.3 kb in size was detected with each probe. These results also indicated that a near full length cDNA clone had been isolated since the hybridization was to a message of the same size as the cDNA.

Figure 4:
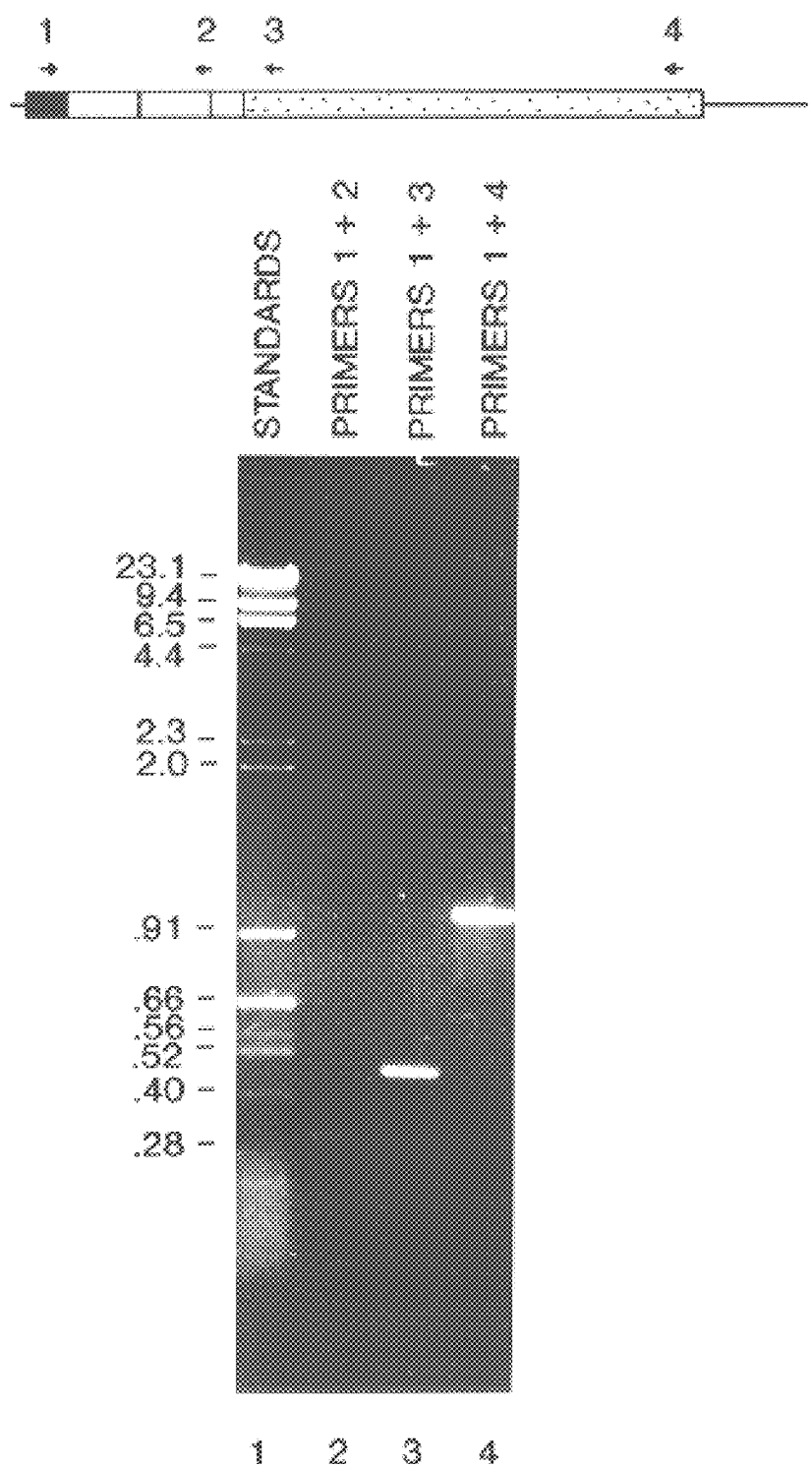

Next, PCR was used to analyze whether the hybridization seen in the RNA gel blot analysis was in fact due to a single mRNA species and not two different messages of approximately the same size. Reverse transcribed total rhizome RNA was used as the template for the PCT. This template would allow discerning the origin of the carboxyl-terminal domain found in uda1. PCR primers corresponded to the beginning of the open reading frame (FIG. 4, #1) (SEQ ID NO:13), the end of the UDA encoding domain (FIG. 4, #2) (SEQ ID NO:14), the beginning of the carboxyl-terminal domain (FIG. 4, #3) (SEQ ID NO:15), and the end of the carboxyl-terminal domain (FIG. 4, #4) (SEQ ID NO:16). An elevated annealing temperature (65° C.) was used for the reactions to obtain highly specific products. FIG. 4 shows that all three sets of primers produced a single predominant PCR product as detected by an ethidium bromide stained agarose gel. The size of each product was exactly as predicted from uda1. Primers 1 and 2 generated a 303 bp product, primers 1 and 3 a 451 bp product and primers 1 and 4 a 995 bp product. The PCR products from each reaction were then subcloned into pUC119 and partially sequenced. In all cases the sequence matched that of uda1. In addition, three partial cDNA clones were independently isolated from an unamplified *U. dioica* rhizome cDNA library using uda1 as a probe. Sequence obtained from these clones matched uda1 sequence.

Comparison of uda1 Deduced Amino Acids to Published Amino Acid Sequence of UDA The deduced amino acid sequence of UDA in uda1 matches the published sequence with a few exceptions (FIG. 5). For the 72 amino acid residues presented by Chapot, et al (Chapot, M-P, Peumans, W. J., and Strosberg, A. D., Extensive homologies between lectins from non-leguminous plants. FEBS Letters 1–95:231–234 (1986)). The remaining five residues would be present at the carboxyl-terminal ends of tryptic fragments only partially sequenced by Chapot, et al (Chapot, M-P, Peumans, W. J., and Strosberg, A. D., Extensive homologies between lectins from non-leguminous plants. FEBS Letters 195:231–234 (1986)).

Comparison of the uda1 Deduced Amino Acid Sequence with Cloned Chitinases

Figure 6:
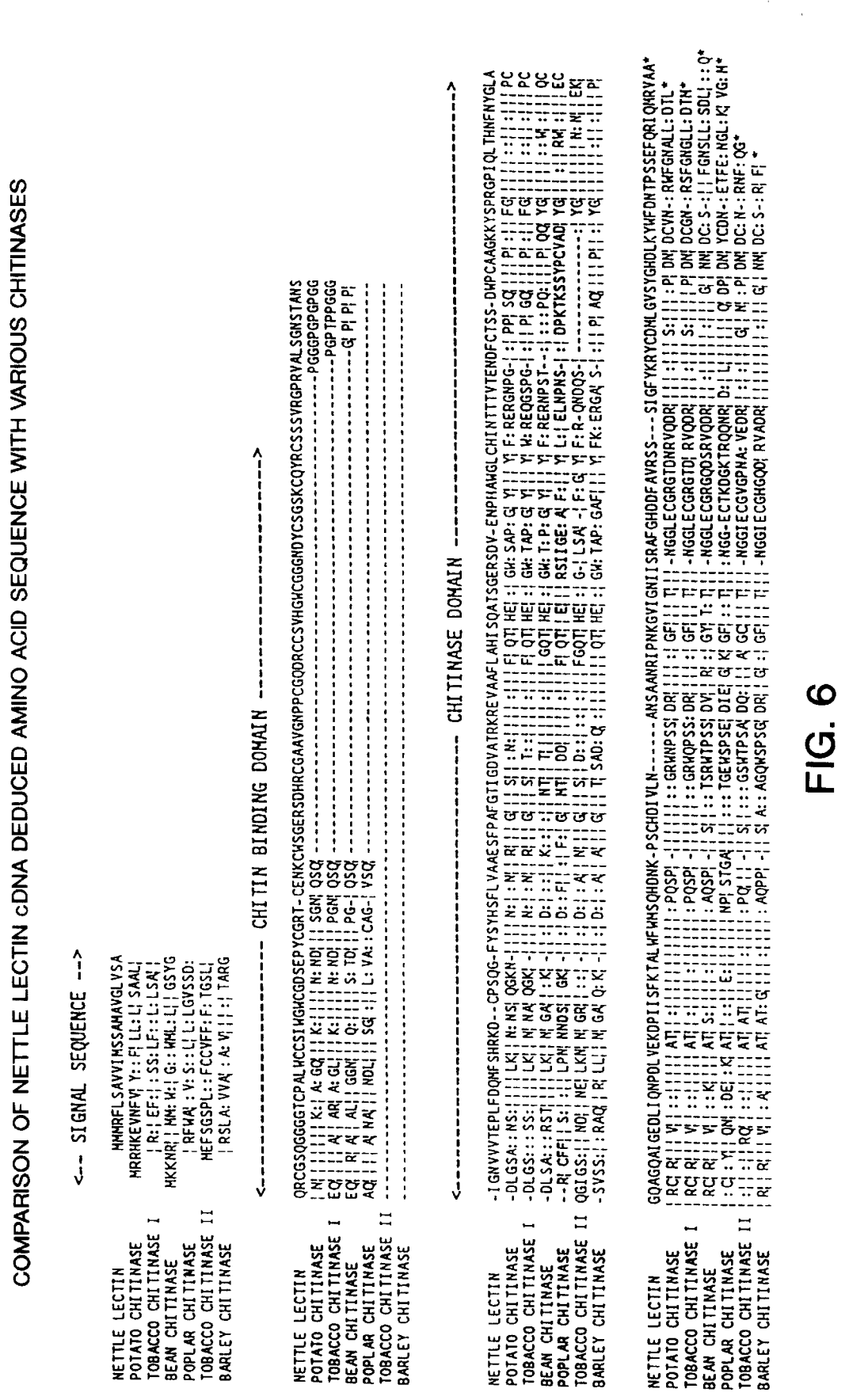

Further analysis of the deduced amino acid sequence from the carboxyl-terminal domain revealed extensive similarity with the deduced amino acid sequence of cloned chitinases (FIG. 6). This similarity extends beyond the chitin-binding domains to include the chitinase catalytic domain. The chitin-binding domain of UDA is approximately twice as long as that seen in the basic (class I) chitinases and hevein. The carboxyl-terminal domain encoded by uda1 has 40–46% identity (approximately 60% with conservative substitutions) with the catalytic domain of the cloned chitinases (FIG. 6). The 'spacer' domain between the chitin-binding and chitinase-like domains has no similarity to previously published sequence for UDA or to the deduced amino acid sequence of the cloned basic chitinases. This 'spacer' region does, however, contain the only potential asparagine (N)-linked oligosaccharide recognition site (N-S-T) at deduced amino acid residue number 100. It remains to be determined whether the UDA precursor is glycosylated or not.

RNA Gel Blot Analysis of *U. dioica* Tissues

Figure 7:
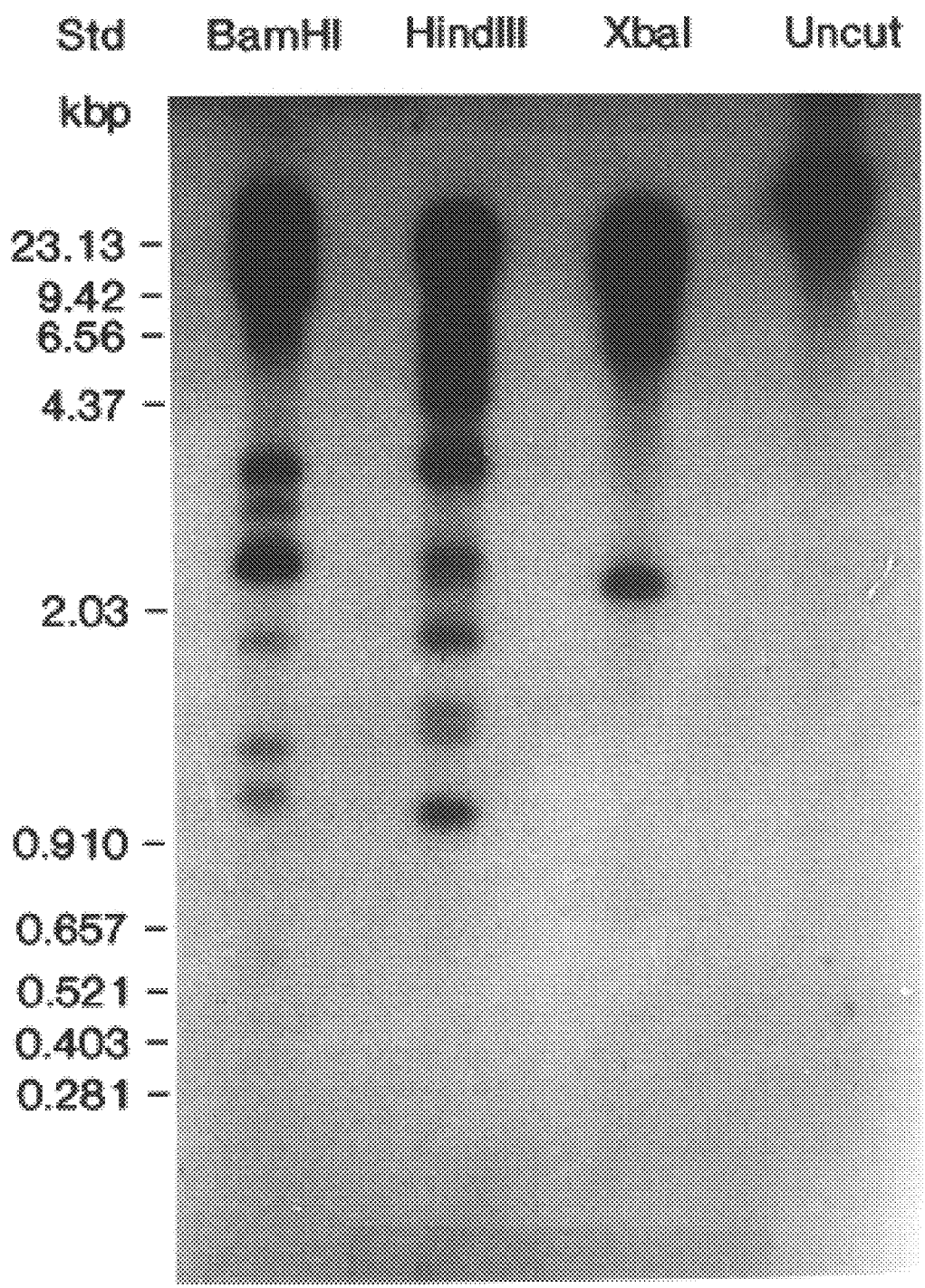

Total RNA isolated from rhizomes, lower and upper stem sections, flower pods with immature seeds, and leaves were examined for the presence of UDA message. Relatively high steady state levels of UDA mRNA were detected in rhizomes and flower pods containing immature seeds (FIG. 7, lanes 1 and 4). These data were expected since UDA has been found only in rhizomes and seeds (Van Damme, E. J. M., and Peumans, W. J., Plant Physiol. 71:328–33 (1987)). In addition, longer exposures of the autoradiograms revealed much lower levels of UDA message in the RNA isolated from the upper portion of the stem. No hybridization was detected with the RNA samples from the lower stem portion or leaf.

Southern Blot Analysis

Figure 8:
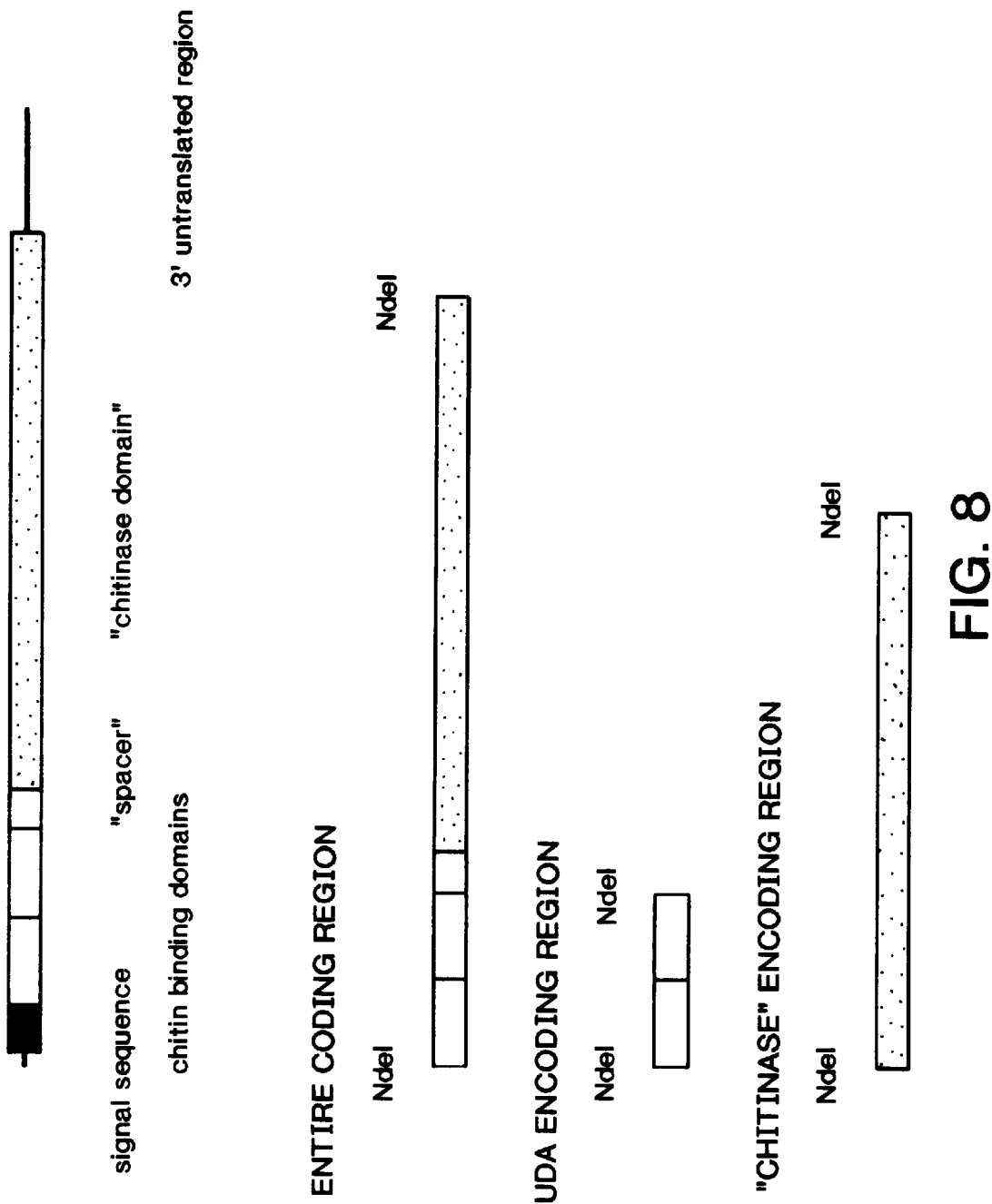
FIG. 8 shows the construction of nettle lectin cDNA for expression in *E. coli.*

Previous studies have reported that UDA in rhizomes of stinging nettle is a complex mixture of isolectins (Van Damme, E. J. M., et al., Plant Physiol. 86:598–601 (1988)). Southern blot analysis of *U. dioica* genomic DNA using uda1 as a probe was performed to analyze whether the reported isolectins could be due to multiple UDA genes. FIG. 8 shows several hybridizing bands with the genomic DNA cleaved with BamHI, HindIII and XbaI. Lanes 1, 2 and 3 contain DNA digested with increasing amounts (16, 80 and 160 units) of BamHI. The identical pattern of hybridizing bands indicates that the digestion in lane 1 was complete and that lane 3 contains at least a 10-fold excess of enzyme. The DNA in lanes 4 and 5 were digested with 160 units of HindIII and XbaI respectively. Since uda1 contains one BamHI restriction site but has no sites for HindIII or XbaI, these data suggests that UDA is encoded by a small multi-gene family. Thus, some of the UDA isolectins may be encoded by independent genes.

Expression of the uDA1 Encoded Domains in *E. coli*

FIG. 8 shows the nettle lectin cDNA mutagenesis constructs for expression in bacteria. To examine activities of the chitin-binding and chitinase-like domains of the nettle lectin three constructs were produced by oligonucleotide directed mutagenesis for expression in E. coli.

The constructs were transcribed under control of the T7 RNA polymerase promotor in the pET expression vector system (Studier, et al., Methods in Enzymology, 185:60 (1990)).

The constructs with the chitin-binding or chitinase-like domains alone both produced large amounts of protein upon induction of the E. coli culture. The construct containing the entire coding region did not produce large amounts of protein but did show enzymatic activity in connection with FIG. 9. The results are shown in FIG. 8.

Figure 9:
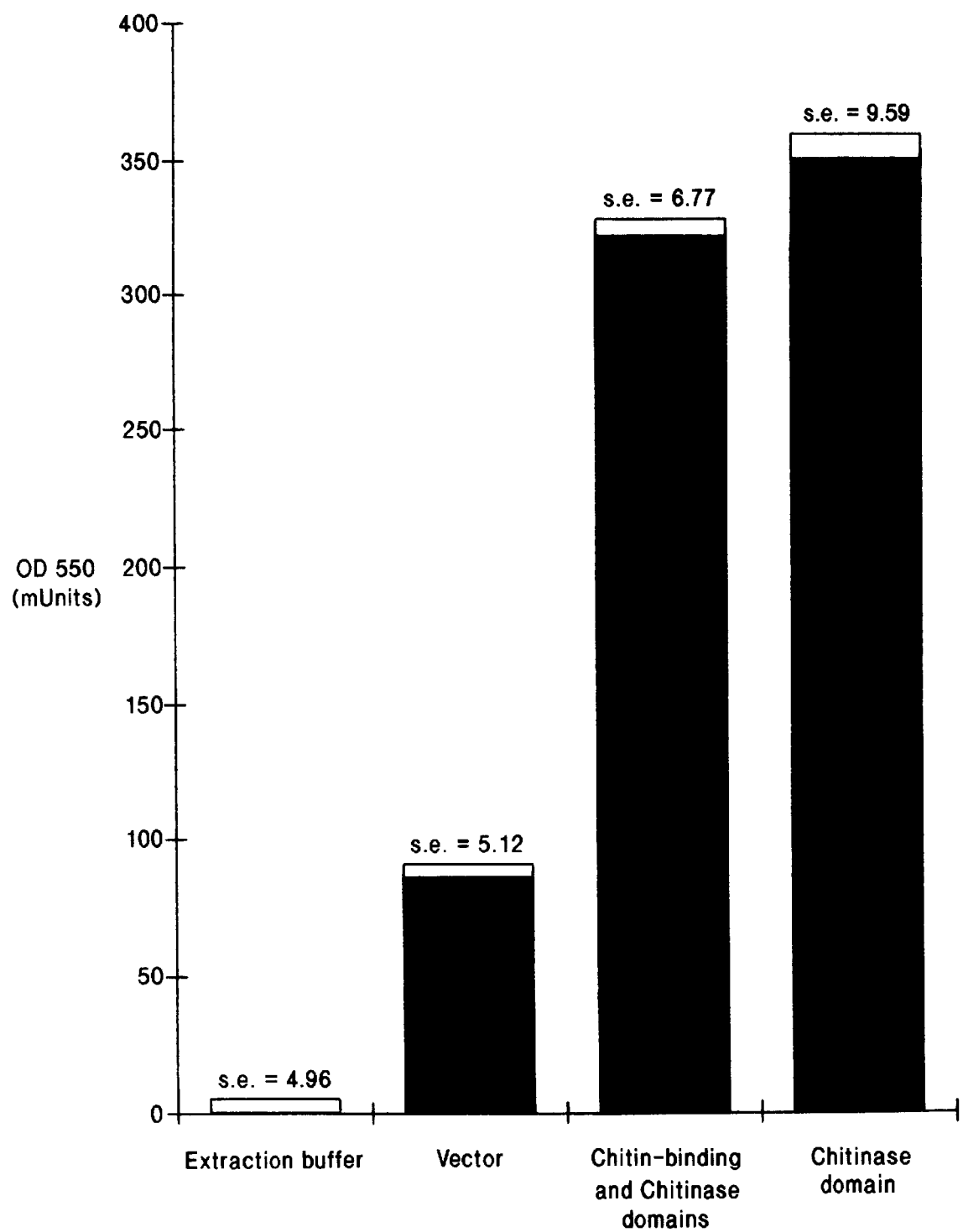
FIG. 9 shows the chitinase activity of the *E. coli* expressed nettle lectin domains.

FIG. 9 shows the chitinase activity of the E. coli expressed nettle lectin domains. A colorimetric chitinase assay of crude E. coli cell extracts was used to analyze activity encoded by the nettle lectin cDNA clone. Both the construct containing the chitinase domain alone and the construct containing the chitinase domain with the chitin-binding domains showed high levels of chitinase activity compared to the control extract (vector alone). FIG. 9 shows the average values from 6 independent reactions with the mean buffer value as zero and the standard error (s.e.) represented as an open box above the activity bar.

Extracts were prepared by resuspending induced culture cells in an extraction buffer, freezing at −20° C., thawing and then clearing the extracts by centrifugation. Each reaction contained the extract from approximately 5 ml of E. coli culture and the chitinase activity shown was normalized for protein concentration. The substrate for these assay was a carboxymethyl-substituted soluble chitin linked to a dye (Remazol Brilliant Violet 5R) (Wirth and Wolf, Journ. of Microbiological Methods, 12:197–205 (1990). The reactions were incubated at RT for 24 hours and the uncleaved substrate precipitated with 1 N HCl on ice and removed by centrifugation.

Discussion

Chitin-binding proteins have been found in a wide variety of plant species. The smallest of these proteins, hevein, is a major protein of rubber tree latex. It consists of a single chitin-binding domain of 43 amino acids (Walujono, K., et al. In Proc. Internatl. Rubber Conf. 518–531 (1975)) and has recently been shown to be synthesized as a preproprotein with an extensive carboxyl-terminal domain unrelated to the chitin-binding domain (Broekaert, W. F., et al., Wound-induced accumulation of mRNA containing a hevein sequence in laticifers of rubber tree (Hevea brasiliensis). Proc. Natl. Acad. Sci. U.S. 87:7633–6737 (1990); and Lee, H., et al., JBC, 266 (1991)). The basic chitinases from tobacco, bean and potato have also been found to consist of a single 43 amino acid chitin-binding domain at the amino-terminal portion of the polypeptide. This is followed by an extensive catalytic domain (Shinshi, H., et al., Regulation of a plant pathogenesis-related enzyme: Inhibition of tissues by auxin and cytokinin. Proc. Natl. Acad. Sci. U.S.A. 84:89–93 (1987)) homologous to the acidic chitinases (Payne, G., et al., Isolation of complementary DNA clones encoding pathogenesis-related proteins P and Q, two acidic chitinases from tobacco. In tobacco these chitinases have been identified as some of the classical pathogenesis related (PR) proteins (Chrispeels, M. J., and N. V. Raikhel, Plant Cell 3:1–9 (1991)). The Gramineae lectins (wheat germ agglutinin (WGA), barley lectin, rice lectin, etc.) contain 4 tandem repeats of the 43 amino acid chitin-binding domain, are found in the embryo and root tips (Raikhel, N. V., et al., Develop. Genetics, in press (1991)) and have insecticidal activities as shown by in vitro experiments (Czapla, T. H. and Lang, B. A., J. Econ. Entomol. 83:2480–2485 (1991)); and Murdock, et al., Phytochemistry 29:85–89 (1990)). These in vitro activities, stress inducible expression, and tissue specific expression all lend support to the hypothesis that these chitin-binding proteins play roles in plant defense (Chrispeels, M. J. and N. V. Raikhel, Plant Cell 3:1–9 (1991)).

The nucleotide and deduced amino acid sequence of UDA, a member of this family of chitin-binding proteins has been described. Initially, PCR was used in an attempt to generate a specific probe for the UDA gene. This strategy involved synthesizing redundant oligonucleotides encompassing all possible codons for several regions of the amino acid sequence. Specific PCR products of the predicted size were obtained from some of these reactions. Subcloning and sequencing the PCR products, however, revealed that with all primer combinations, only primer/primer products had been made. In retrospect it is clear that these results were due to the highly G/C rich nature of the UDA gene. In addition to base composition of the primers, it appeared from the deduced amino acid sequence of uda1 that a tryptic fragment, to which some of the primers were made, had been misplaced. Thus PCR primers to this region would be lead to DNA synthesis away from the opposing primers and subsequently preventing amplification.

Chemical synthesis of a gene based on extensive amino acid sequence has been successfully used to generate a specific gene probe (Beremand, P. D., et al., Archives of Biochem. and Biophysics, 256:90–120 (1987)). Although complete amino acid sequence was not available for UDA, homology between UDA and other chitin-binding proteins permitted us to design the oligonucleotides. The resulting synthetic gene was approximately 72% identical with the nucleotide sequence of uda1. This level of identity allowed sufficient specificity for screening the cDNA library at medium stringency.

The cDNA clone isolated with the synthetic UDA gene had an unexpected structure. Along with the anticipated region encoding UDA and a putative signal sequence at the 5' end, the open reading frame possessed an additional 263 amino acids. Four lines of evidence show that the cDNA isolated is the correct gene for UDA. First, the deduced amino acids of the UDA encoding domain of uda1 match 68 of 72 amino acids sequenced from UDA tryptic fragments (Chapot, M-P, et al., Extensive homologies between lectins from non-leguminous plants. FEBS Letters 195:231–234 (1986)) (FIG. 3). Second, RNA gel blot analysis (FIG. 4) shows that both the UDA encoding region and the carboxyl-terminal region hybridize to a single mRNA species similar to the size of uda1 (1300 bp). Third, PCR analysis of reverse transcribed (oligo-dT primed) total rhizome RNA shows that the UDA encoding domain and the carboxyl-terminal domain exist on the same mRNA species. Finally, independently isolated uDA cDNA cones from an unamplified library exactly match the sequence of uda1.

All of the previously cloned genes for chitin-binding proteins seem to be the result of either chitin-binding domain duplications (Gramineae lectins) or fusions with unrelated domains (hevein and basic chitinases) (Chrispeels, M. J., et al., Plant Cell 3:1–9 (1991)). The UDA is the first example of a chitin-binding protein gene resulting from both a domain duplication and fusion with an unrelated domain. Differences between the deduced amino acid sequence of uda1 and previous amino acid sequence of UDA tryptic fragments (Chapot, M-P., et al., Extensive homologies between lectins from non-leguminous plants. FEBS Letters 195:231–234 (1986)) are most probably due to variations between isolectins. UDA has been shown to have up to seven isoforms (Van Damme, E. J. M., et al., Plant Physiol. 86:598–601 (1988)). It is also possible that mistakes arose in amino acid sequencing since the majority of the differences lie on a single tryptic fragment.

The chitinase-like encoding domain of uda1 remains enigmatic both as to its function and processing. The deduced amino acids for the carboxyl-terminal domain possess approximately 60% similarity with the catalytic domain of other cloned chitinases. These chitinases, however, are over 90% similar to each other. Whether or not the uda1 encoded protein has chitinase activity remains to be determined. Where studied, it is known that the basic chitinases do not undergo a processing event to release the chitin-binding domain from the chitinase catalytic domain. Presumably this type of processing event does occur with the uda1 encoded protein since UDA, when isolated from the plant, is a very small protein (8.5 kDa) possessing only the two chitin-binding domains. Lee, H. I., et al., JBC, 266 (1991)) have shown that the hevein preproprotein is processed in vivo to yield the chitin-binding protein (hevein, 5 kDa) and a polypeptide of unknown function (16 kDa). The Gramineae lectins have also been shown to undergo post-translational processing of the carboxyl-terminal propeptide with 14 to 27 amino acids removed (Raikhel, N. V., et al., Develop. Genects, in press (1991)). Differences between the uda1 encoded 'spacer' region and the 'hinge' region of the cloned basic chitinases suggests that there may be differences in their functions. The chitinase 'hinge' region tends to be short, 8 to 11 residues, and rich in proline and glycine while the 'spacer' region of the uda1 deduced amino acid sequence was longer, 19 residues, and contained only one proline. Since the basic chitinases are not known to undergo a cleavage to remove the chitin-binding domain it is likely this 'spacer' region in the UDA proprotein contains the recognition site for the proteolytic cleavage.

The plant defense functions of the chitin-binding proteins allows for enhancement of plant disease resistance by overexpression of these proteins in transgenic plants. It has been shown that increasing the chitinase activity in transgenic plants by overexpression of a chitinase in tobacco had no discernable effect on fungal resistance (Broglie, K. E., et al., Proc. Natl. Acad. Sci. U.S.A. 83:6820–6824 (1986)). However, Broekaert, W. F., et al., Science 245:1100–1102 (1989)) has shown that UDA and chitinase have different modes of action for inhibition of fungal growth in vitro. In addition, UDA acts synergistically with chitinase for inhibiting fungal growth in vitro. These data suggest that expression of UDA in transgenic plants can enhance resistance to fungal pathogens where expression of chitinase did not.

Attached is Appendix I showing Sequence ID NOS. 1 and 2.

It is intended that the foregoing description be only illustrative of the present invention and that the present invention be limited only by the hereinafter appended claims.

I claim:

1. A DNA encoding a chitin binding protein of rhizomes of *Urtica dioica* comprising the sequence as set forth in SEQ ID NO:1 or subunits of SEQ ID NO:1 which encode a peptide which is chitin binding.

2. The DNA of claim 1 linked to a second DNA encoding a chitinase protein comprising a sequence as set forth in SEQ ID NO:1.

3. A DNA encoding a chitin binding peptide comprising the sequence between 91 and 348 as set forth in Sequence ID NO:1.

4. A DNA comprising the sequence as set forth in Sequence ID NO:1 encoding a chitin binding peptide, a chitinase and a signal peptide.

5. The DNA of claim 1 operably linked to a promoter DNA wherein the promoter DNA is functional in *E. coli*.

6. The DNA of claim 5 wherein the promoter DNA is a tandem duplicated cauliflower mosaic virus 35S promoter.

7. The DNA of claim 5 linked to a chitinase protein encoding DNA.

8. A vector comprising DNA encoding a chitin binding peptide of rhizomes of *Urtica dioica* comprising a sequence as set forth in SEQ ID NO:1 or subunits of SEQ ID NO:1 encoding a smaller peptide which is chitin binding operably linked to a promoter DNA which is functional in *E. coli*.

9. The vector DNA of claim 8 wherein the DNA is linked to a chitinase protein encoding DNA comprising the sequence as set forth in SEQ ID NO:1.

10. A vector DNA linked to DNA encoding a chitin binding peptide comprising the sequence between 91 and 348 as set forth in Sequence ID NO: 1.

11. A vector DNA comprising cDNA encoding a chitin binding peptide comprising the sequence as set forth in Sequence ID NO: 1 operably linked to another DNA encoding a chitin binding peptide, a chitinase-like protein and a signal protein, wherein the vector DNA is functional in *E. coli*.

12. The vector DNA of claim 8 wherein the DNA is operably linked to a promoter DNA for the DNA which promotes expression in the *E. coli* and is in an expression vector for expression of the DNA.

13. The vector DNA of claim 12 wherein the promoter is a tandem duplicated cauliflower mosaic virus 35S promoter.

14. A transgenic plant having incorporated into its genome a DNA construct encoding a chitin binding peptide of rhizomes of *Urtica dioica* comprising the sequence as set forth in SEQ ID NO:1 or subunits of the DNA which encode a protein which is chitin binding operably linked to a promoter DNA which produces expression of the protein in the plant.

15. The transgenic plant of claim 14 wherein the DNA encodes a chitin binding protein comprising the sequence between 22 and 1137 as set forth in Sequence ID NO: 1.

16. The transgenic plant of claim 14 comprising the sequence as set forth in Sequence ID NO: 1 encoding a chitin binding protein, a chitinase-like protein and a signal protein.

17. The transgenic plant of claim 14 wherein the promoter DNA is a tandem duplicated cauliflower mosaic virus 35S promoter.

18. The transgenic plant of claim 14 which is a monocot.

19. The transgenic plant of claim 14 which is a dicot.

20. The transgenic plant of claim 14 wherein the DNA is operably linked to another DNA encoding a chitinase protein.

21. The transgenic plant of claim 17 wherein the DNA construct is operably linked to a chitinase protein encoding DNA having a sequence as set forth in SEQ ID NO: 1.

22. A synthetic gene comprising the sequence of 219 nucleotides as follows:

```
CAG AGG TGC GGA TCT CAA GGA GGT GGC GGA ACT TGC CCT GCT CTT AGG     48
Gln Arg Cys Gly Ser Gln Gly Gly Gly Thr Cys Pro Ala Leu Arg
 1           5                   10                  15

TGT TGC AGC ATT TGG GGA TGG TGT GGA GCT AGC AGC CCA TAT TGT GGC     96
Cys Cys Ser Ile Trp Gly Trp Cys Gly Ala Ser Ser Pro Tyr Cys Gly
             20                  25                  30

AAG GGA TGC CAG TAC AGA TGC TGG AGC GGA GAA AGA TGC GGA GCT CAA    144
Lys Gly Cys Gln Tyr Arg Cys Trp Ser Gly Glu Arg Cys Gly Ala Gln
         35                  40                  45

GTT GGA AAC CCA ACT TGC GGA CAA CTT AGG TGT TGC AGC GTT CAT GGG    192
Val Gly Asn Pro Thr Cys Gly Gln Leu Arg Cys Cys Ser Val His Gly
     50                  55                  60

TGG TGT GGA GGA GGT AAT GAC TAT TGT                                219
Trp Cys Gly Gly Gly Asn Asp Tyr Cys
``` as set forth in SEQ ID NO: 2.

* * * * *

UNITED STATES PATENT AND TRADEMARK OFFICE
CERTIFICATE OF CORRECTION

PATENT NO. : 6,133,507
DATED : 10/17/2000
INVENTOR(S) : Raikhel

It is certified that error appears in the above-identified patent and that said Letters Patent is hereby corrected as shown below:

Column 2, line 16, delete "Figure 2b is" and insert --Figures 2b-1 and 2b-2 are--

Column 9, line 14, delete "(Fig. 2)" and insert --Figures 2b-1 and 2b-2--

Signed and Sealed this

Nineteenth Day of December, 2000

Attest:

Q. TODD DICKINSON

*Attesting Officer*      *Commissioner of Patents and Trademarks*

SEQUENCE LISTING

<160> NUMBER OF SEQ ID NOS: 19

<210> SEQ ID NO 1
<211> LENGTH: 1317
<212> TYPE: DNA
<213> ORGANISM: Urtica dioica

<400> SEQUENCE: 1

```
aatcatagta agaaagaaaa gatgatgatg aggtttttat ctgccgtagt gatcatgtcc      60
tccgctatgg cggtgggtct agtgtcggca cagaggtgcg gaagccaagg cggcggggt     120 acgtgtcccg ccttgtggtg ctgcagcatc tggggctggt gcggcgactc ggagccctac    180
tgcggccgca cctgcgagaa caagtgctgg agcggcgagc ggtcggacca ccgctgcggc    240
gccgctgtag gaaaccctcc gtgcggccag gaccggtgct gcagcgtcca cgggtggtgc    300
ggtggcggca acgactactg ctccgggagc aaatgccagt accgctgctc ctcctccgtc    360
cgtggacccc gcgtcgctct cagcggcaat tccaccgcca actccatcgg caacgtcgtc    420
gtcaccgagc cgctgttcga ccagatgttc tcccaccgca aggactgtcc gagccagggc    480
ttctacagct accactcctt cctcgtagcc gccgagtcct tcccagcttt cgggaccatc    540
ggagatgttg cgacacgcaa gagagaggtc gcagcgttcc tcgcccatat ctcccaagca    600
acatcagggg aaaggtctga cgtggaaaac cctcatgcat gggggctttg tcatatcaat    660
```

```
acaactactg tgactgagaa tgacttctgt acctcctccg actggccttg cgctgccggc    720
aaaaaataca gccctcgagg acccatccag ctcacccaca acttcaacta cggacttgcc    780
ggccaagcca ttggagagga cctgattcag aaccctgact tggtagaaaa ggatccaatc    840
atatcattca agacggcctt gtggttctgg atgtcccagc acgacaacaa accttcatgc    900
catgacattg tcctcaatgc caactccgcc gcgaacagaa tcccaaacaa aggtgtgatc    960
ggcaacatta ttagccgcgc ttttgggcac gacgactttg ccgttagatc ttcaagcatc   1020
ggattttaca agaggtactg cgacatgctg ggagtgagct atggacatga cttgaagtac   1080
tggttcgata acactccatc atcggagttc aacgcatcc aaatgcgtgt tgcggcgtaa    1140
aacaagctag tcctccccaa gtggctctct agtagtaaga gtagctctct catagcgaga   1200
gagcggcatg ttgaatccct gttatgctat gtaatattat gttacgcatg tatgttagaa   1260
acatatatgt gtgattttct agctcttacg agttataaat aaagtagcca ctttcct     1317
```

<210> SEQ ID NO 2
<211> LENGTH: 219
<212> TYPE: DNA
<213> ORGANISM: Artificial Sequence
<220> FEATURE:
<223> OTHER INFORMATION: Description of Artificial Sequence:  DNA
      fragment containing parts of the UDA gene used as a probe
      for the UDA gene.

<400> SEQUENCE: 2

```
cagaggtgcg gatctcaagg aggtggcgga acttgccctg ctcttaggtg ttgcagcatt     60
tggggatggt gtggagctag cagcccatat tgtggcaagg gatgccagta cagatgctgg    120
agcggagaaa gatgcggagc tcaagttgga aacccaactt gcggacaact taggtgttgc    180
agcgttcatg ggtggtgtgg aggaggtaat gactattgt                           219
```

<210> SEQ ID NO 3
<211> LENGTH: 83
<212> TYPE: PRT
<213> ORGANISM: Artificial Sequence
<220> FEATURE:
<223> OTHER INFORMATION: Description of Artificial Sequence: Amino acid
      sequence encoded by the artificial DNA in SEQ ID
      NO:2.

<400> SEQUENCE: 3

```
Gln Arg Cys Gly Ser Gln Gly Gly Gly Thr Cys Pro Ala Leu Arg
  1               5                  10                  15

Cys Cys Ser Ile Trp Gly Trp Cys Gly Ala Ser Ser Pro Trp Cys Gly
             20                  25                  30

Ala Ser Ser Pro Tyr Cys Gly Lys Gly Cys Gln Tyr Arg Cys Trp Ser
         35                  40                  45

Gly Glu Arg Cys Gly Ala Gln Val Gly Asn Pro Thr Cys Gly Gln Leu
     50                  55                  60

Arg Cys Cys Arg Cys Cys Ser Val His Gly Trp Cys Gly Gly Gly Asn
 65                  70                  75                  80

Asp Tyr Cys
```

<210> SEQ ID NO 4
<211> LENGTH: 372
<212> TYPE: PRT
<213> ORGANISM: Urtica dioica

<400> SEQUENCE: 4

```
Met Met Met Arg Phe Leu Ser Ala Val Val Ile Met Ser Ser Ala Met
 1               5                  10                  15

Ala Val Gly Leu Val Ser Ala Gln Arg Cys Gly Ser Gln Gly Gly Gly
            20                  25                  30

Gly Thr Cys Pro Ala Leu Trp Cys Cys Ser Ile Trp Gly Trp Cys Gly
         35                  40                  45

Asp Ser Glu Pro Tyr Cys Gly Arg Thr Cys Glu Asn Lys Cys Trp Ser
     50                  55                  60

Gly Glu Arg Ser Asp His Arg Cys Gly Ala Ala Val Gly Asn Pro Pro
 65                  70                  75                  80

Cys Gly Gln Asp Arg Cys Cys Ser Val His Gly Trp Cys Gly Gly Gly
                 85                  90                  95

Asn Asp Tyr Cys Ser Gly Ser Lys Cys Gln Tyr Arg Cys Ser Ser Ser
             100                 105                 110

Val Arg Gly Pro Arg Val Ala Leu Ser Gly Asn Ser Thr Ala Asn Ser
         115                 120                 125

Ile Gly Asn Val Val Thr Glu Pro Leu Phe Asp Gln Met Phe Ser
 130                 135                 140

His Arg Lys Asp Cys Pro Ser Gln Gly Phe Tyr Ser Tyr His Ser Phe
145                 150                 155                 160

Leu Val Ala Ala Glu Ser Phe Pro Ala Phe Gly Thr Ile Gly Asp Val
                 165                 170                 175

Ala Thr Arg Lys Arg Glu Val Ala Ala Phe Leu Ala His Ile Ser Gln
             180                 185                 190

Ala Thr Ser Gly Glu Arg Ser Asp Val Glu Asn Pro His Ala Trp Gly
         195                 200                 205

Leu Cys His Ile Asn Thr Thr Thr Val Thr Glu Asn Asp Phe Cys Thr
210                 215                 220

Ser Ser Asp Trp Pro Cys Ala Ala Gly Lys Lys Tyr Ser Pro Arg Gly
225                 230                 235                 240

Pro Ile Gln Leu Thr His Asn Phe Asn Tyr Gly Leu Ala Gly Gln Ala
                 245                 250                 255

Ile Gly Glu Asp Leu Ile Gln Asn Pro Asp Leu Val Glu Lys Asp Pro
             260                 265                 270

Ile Ile Ser Phe Lys Thr Ala Leu Trp Phe Trp Met Ser Gln His Asp
         275                 280                 285

Asn Lys Pro Ser Cys His Asp Ile Val Leu Asn Ala Asn Ser Ala Ala
     290                 295                 300

Asn Arg Ile Pro Asn Lys Gly Val Ile Gly Asn Ile Ile Ser Arg Ala
305                 310                 315                 320

Phe Gly His Asp Asp Phe Ala Val Arg Ser Ser Ile Gly Phe Tyr
                 325                 330                 335

Lys Arg Tyr Cys Asp Met Leu Gly Val Ser Tyr Gly His Asp Leu Lys
             340                 345                 350

Tyr Trp Phe Asp Asn Thr Pro Ser Ser Glu Phe Gln Arg Ile Gln Met
         355                 360                 365

Arg Val Ala Ala
370

<210> SEQ ID NO 5
<211> LENGTH: 328
<212> TYPE: PRT
<213> ORGANISM: Solanum tuberosum
```

-continued

```
<400> SEQUENCE: 5

Met Arg Arg His Lys Glu Val Asn Phe Val Ala Tyr Leu Leu Phe Ser
 1               5                   10                  15

Leu Leu Val Leu Val Ser Ala Ala Leu Ala Gln Asn Cys Gly Ser Gln
             20                  25                  30

Gly Gly Gly Lys Ala Cys Ala Ser Gly Gln Cys Cys Ser Lys Phe Gly
         35                  40                  45

Trp Cys Gly Asn Thr Asn Asp Tyr Cys Gly Ser Gly Asn Cys Gln Ser
     50                  55                  60

Gln Cys Pro Gly Gly Pro Gly Pro Gly Pro Gly Gly Asp Leu Gly
 65                  70                  75                  80

Ser Ala Ile Ser Asn Ser Met Phe Asp Gln Met Leu Lys His Arg Asn
             85                  90                  95

Glu Asn Ser Cys Gln Gly Lys Asn Phe Tyr Ser Tyr Asn Ala Phe Ile
            100                 105                 110

Asn Ala Ala Arg Ser Phe Pro Gly Phe Gly Thr Ser Gly Asp Ile Asn
            115                 120                 125

Ala Arg Lys Arg Glu Ile Ala Ala Phe Phe Ala Gln Thr Ser His Glu
        130                 135                 140

Thr Thr Gly Gly Trp Ala Ser Ala Pro Asp Gly Pro Tyr Ala Trp Gly
145                 150                 155                 160

Tyr Cys Phe Leu Arg Glu Arg Gly Asn Pro Gly Asp Tyr Cys Pro Pro
                165                 170                 175

Ser Ser Gln Trp Pro Cys Ala Pro Gly Arg Lys Tyr Phe Gly Arg Gly
            180                 185                 190

Pro Ile Gln Ile Ser His Asn Tyr Asn Tyr Gly Pro Cys Gly Arg Ala
        195                 200                 205

Ile Gly Val Asp Leu Leu Asn Asn Pro Asp Leu Val Ala Thr Asp Pro
210                 215                 220

Val Ile Ser Phe Lys Thr Ala Leu Trp Phe Trp Met Thr Pro Gln Ser
225                 230                 235                 240

Pro Lys Pro Ser Cys His Asp Val Ile Ile Gly Arg Trp Asn Pro Ser
                245                 250                 255

Ser Ala Asp Arg Ala Ala Asn Arg Leu Pro Gly Phe Gly Val Ile Thr
            260                 265                 270

Asn Ile Ile Asn Gly Gly Leu Glu Cys Gly Arg Gly Thr Asp Asn Arg
        275                 280                 285

Val Gln Asp Arg Ile Gly Phe Tyr Arg Arg Tyr Cys Ser Ile Leu Gly
    290                 295                 300

Val Thr Pro Gly Asp Asn Leu Asp Cys Val Asn Gln Arg Trp Phe Gly
305                 310                 315                 320

Asn Ala Leu Leu Val Asp Thr Leu
                325

<210> SEQ ID NO 6
<211> LENGTH: 310
<212> TYPE: PRT
<213> ORGANISM: Nicotiana tabacum

<400> SEQUENCE: 6

Ser Leu Leu Leu Leu Ser Ala Ser Ala Glu Gln Cys Gly Ser Gln Ala
 1               5                  10                  15

Gly Gly Ala Arg Cys Ala Ser Gly Leu Cys Cys Ser Lys Phe Gly Trp
             20                  25                  30
```

Cys Gly Asn Thr Asn Asp Tyr Cys Gly Pro Asn Cys Gln Ser Gln
            35                  40                  45

Cys Pro Gly Gly Pro Thr Pro Pro Gly Gly Asp Leu Gly Ser Ile
 50                  55                  60

Ile Ser Ser Ser Met Phe Asp Gln Met Leu Lys His Arg Asn Asp Asn
 65                  70                  75                  80

Ala Cys Gln Gly Lys Gly Phe Tyr Ser Tyr Asn Ala Phe Ile Asn Ala
                 85                  90                  95

Ala Arg Ser Phe Pro Gly Phe Gly Thr Ser Gly Asp Thr Thr Ala Arg
                100                 105                 110

Lys Arg Glu Ile Ala Ala Phe Phe Ala Gln Thr Ser His Glu Thr Thr
            115                 120                 125

Gly Gly Trp Ala Thr Ala Pro Asp Gly Pro Tyr Ala Trp Gly Tyr Cys
130                 135                 140

Trp Leu Arg Glu Gln Gly Ser Pro Gly Asp Tyr Cys Thr Pro Ser Gly
145                 150                 155                 160

Gln Trp Pro Cys Ala Pro Gly Arg Lys Tyr Phe Gly Arg Gly Pro Ile
                165                 170                 175

Gln Ile Ser His Asn Tyr Asn Tyr Gly Pro Cys Gly Arg Ala Ile Gly
                180                 185                 190

Val Asp Leu Leu Asn Asn Pro Asp Leu Val Ala Thr Asp Pro Val Ile
            195                 200                 205

Ser Phe Lys Ser Ala Leu Trp Phe Trp Met Thr Pro Gln Ser Pro Lys
210                 215                 220

Pro Ser Cys His Asp Val Ile Ile Gly Arg Trp Gln Pro Ser Ser Ala
225                 230                 235                 240

Asp Arg Ala Ala Asn Arg Leu Pro Gly Phe Gly Val Ile Thr Asn Ile
                245                 250                 255

Ile Asn Gly Gly Leu Glu Cys Gly Arg Gly Thr Asp Ser Arg Val Gln
                260                 265                 270

Asp Arg Ile Gly Phe Tyr Arg Arg Tyr Cys Ser Ile Leu Gly Val Ser
            275                 280                 285

Pro Gly Asp Asn Leu Asp Cys Gly Asn Gln Arg Ser Phe Gly Asn Gly
290                 295                 300

Leu Leu Val Asp Thr Met
305                 310

<210> SEQ ID NO 7
<211> LENGTH: 328
<212> TYPE: PRT
<213> ORGANISM: Phaseolus vulgaris

<400> SEQUENCE: 7

Met Lys Lys Asn Arg Met Met Met Ile Trp Ser Val Gly Val Val
 1               5                  10                  15

Trp Met Leu Leu Leu Val Gly Gly Ser Tyr Gly Glu Gln Cys Gly Arg
            20                  25                  30

Gln Ala Gly Gly Ala Leu Cys Pro Gly Gly Asn Cys Cys Ser Gln Phe
                35                  40                  45

Gly Trp Cys Gly Ser Thr Thr Asp Tyr Cys Gly Pro Gly Cys Gln Ser
 50                  55                  60

Gln Cys Gly Gly Pro Ser Pro Ala Pro Thr Asp Leu Ser Ala Leu Ile
 65                  70                  75                  80

Ser Arg Ser Thr Phe Asp Gln Met Leu Lys His Arg Asn Asp Gly Ala
                85                  90                  95

Cys Pro Ala Lys Gly Phe Tyr Thr Tyr Asp Ala Phe Ile Ala Ala Ala
            100                 105                 110

Lys Ala Tyr Pro Ser Phe Gly Asn Thr Gly Asp Thr Ala Thr Arg Lys
        115                 120                 125

Arg Glu Ile Ala Ala Phe Leu Gly Gln Thr Ser His Glu Thr Thr Gly
    130                 135                 140

Gly Trp Ala Thr Ala Pro Asp Gly Pro Tyr Ala Trp Gly Tyr Cys Phe
145                 150                 155                 160

Val Arg Glu Arg Asn Pro Ser Thr Tyr Cys Ser Ala Thr Pro Gln Phe
                165                 170                 175

Pro Cys Ala Pro Gly Gln Gln Tyr Tyr Gly Arg Gly Pro Ile Gln Ile
            180                 185                 190

Ser Trp Asn Tyr Asn Tyr Gly Gln Cys Gly Arg Ala Ile Gly Val Asp
        195                 200                 205

Leu Leu Asn Lys Pro Asp Leu Val Ala Thr Asp Ser Val Ile Ser Phe
    210                 215                 220

Lys Ser Ala Leu Trp Phe Trp Met Thr Ala Gln Ser Pro Lys Pro Ser
225                 230                 235                 240

Ser His Asp Val Ile Thr Ser Arg Trp Thr Pro Ser Ser Ala Asp Val
                245                 250                 255

Ala Ala Arg Arg Leu Pro Gly Tyr Gly Thr Val Thr Asn Ile Ile Asn
            260                 265                 270

Gly Gly Leu Glu Cys Gly Arg Gly Gln Asp Ser Arg Val Gln Asp Arg
        275                 280                 285

Ile Gly Phe Phe Lys Arg Tyr Cys Asp Leu Leu Gly Val Gly Tyr Gly
    290                 295                 300

Asn Asn Leu Asp Cys Tyr Ser Gln Thr Pro Phe Gly Asn Ser Leu Leu
305                 310                 315                 320

Leu Ser Asp Leu Val Thr Ser Gln
                325

<210> SEQ ID NO 8
<211> LENGTH: 316
<212> TYPE: PRT
<213> ORGANISM: Populus balsamifera subsp. trichocarpa X Populus
      deltoides

<400> SEQUENCE: 8

Met Arg Phe Trp Ala Leu Thr Val Leu Ser Leu Leu Ser Leu Leu
 1               5                  10                  15

Leu Gly Val Ser Ser Asp Thr Ala Gln Cys Gly Ser Gln Ala Gly Asn
            20                  25                  30

Ala Thr Cys Pro Asn Asp Leu Cys Cys Ser Ser Gly Gly Tyr Cys Gly
        35                  40                  45

Leu Thr Val Ala Tyr Cys Cys Ala Gly Cys Val Ser Gln Cys Arg Asn
    50                  55                  60

Cys Phe Phe Thr Glu Ser Met Phe Glu Gln Met Leu Pro Asn Arg Asn
65                  70                  75                  80

Asn Asp Ser Cys Pro Gly Lys Gly Phe Tyr Thr Tyr Asp Ala Tyr Phe
                85                  90                  95

Val Ala Thr Glu Phe Tyr Pro Gly Phe Gly Met Thr Gly Asp Asp Asp
            100                 105                 110

Thr Arg Lys Arg Glu Leu Ala Ala Phe Phe Ala Gln Thr Ser Gln Glu
        115                 120                 125

```
Thr Ser Gly Arg Ser Ile Ile Gly Glu Asp Ala Pro Phe Thr Trp Gly
    130                 135                 140
Tyr Cys Leu Val Asn Glu Leu Asn Pro Asn Ser Asp Tyr Cys Asp Pro
145                 150                 155                 160
Lys Thr Lys Ser Ser Tyr Pro Cys Val Ala Asp Tyr Tyr Gly Arg Gly
                165                 170                 175
Pro Leu Gln Leu Arg Trp Asn Tyr Asn Tyr Gly Glu Cys Gly Asn Tyr
            180                 185                 190
Leu Gly Gln Asn Leu Leu Asp Glu Pro Glu Lys Val Ala Thr Asp Pro
        195                 200                 205
Val Leu Ser Phe Glu Ala Ala Leu Trp Phe Trp Met Asn Pro His Ser
    210                 215                 220
Thr Gly Ala Pro Ser Cys His Glu Val Ile Thr Gly Glu Trp Ser Pro
225                 230                 235                 240
Ser Glu Ala Asp Ile Glu Ala Gly Arg Lys Pro Gly Phe Gly Met Leu
                245                 250                 255
Thr Asn Ile Ile Thr Asn Gly Gly Glu Cys Thr Lys Asp Gly Lys Thr
            260                 265                 270
Arg Gln Gln Asn Arg Ile Asp Tyr Tyr Leu Arg Tyr Cys Asp Met Leu
        275                 280                 285
Gln Val Asp Pro Gly Asp Asn Leu Tyr Cys Asp Asn Gln Glu Thr Phe
    290                 295                 300
Glu Asp Asn Gly Leu Leu Lys Met Val Gly Thr Met
305                 310                 315

<210> SEQ ID NO 9
<211> LENGTH: 253
<212> TYPE: PRT
<213> ORGANISM: Nicotiana tabacum

<400> SEQUENCE: 9

Met Glu Phe Ser Gly Ser Pro Leu Thr Leu Phe Cys Cys Val Phe Phe
  1               5                  10                  15
Leu Phe Leu Thr Gly Ser Leu Ala Gln Gly Ile Gly Ser Ile Val Thr
            20                  25                  30
Asn Asp Leu Phe Asn Glu Met Leu Lys Asn Arg Asn Asp Gly Arg Cys
        35                  40                  45
Pro Ala Asn Gly Phe Tyr Thr Tyr Asp Ala Phe Ile Ala Ala Ala Asn
    50                  55                  60
Ser Phe Pro Gly Phe Gly Thr Ser Gly Asp Asp Thr Ala Arg Arg Lys
65                  70                  75                  80
Glu Ile Ala Ala Phe Phe Gly Gln Thr Ser His Glu Thr Thr Gly Gly
                85                  90                  95
Ser Leu Ser Ala Glu Pro Phe Thr Gly Gly Tyr Cys Phe Val Arg Gln
            100                 105                 110
Asn Asp Gln Ser Asp Arg Tyr Tyr Gly Arg Gly Pro Ile Gln Leu Thr
        115                 120                 125
Asn Gln Asn Asn Tyr Glu Lys Ala Gly Asn Ala Ile Arg Gln Asp Leu
    130                 135                 140
Val Asn Asn Pro Asp Leu Val Ala Thr Asp Ala Thr Ile Ser Phe Lys
145                 150                 155                 160
Thr Ala Ile Trp Phe Trp Met Thr Pro Gln Asp Asn Lys Pro Ser Ser
                165                 170                 175
His Asp Val Ile Ile Gly Ser Trp Thr Pro Ser Ala Ala Asp Gln Ser
            180                 185                 190
```

```
Ala Asn Arg Ala Pro Gly Cys Gly Val Ile Thr Asn Ile Ile Asn Gly
            195                 200                 205

Gly Ile Glu Cys Gly Val Gly Pro Asn Ala Ala Val Glu Asp Arg Ile
        210                 215                 220

Gly Tyr Tyr Arg Arg Tyr Cys Gly Met Leu Asn Val Ala Pro Gly Asp
225                 230                 235                 240

Asn Leu Asp Cys Tyr Asn Gln Arg Asn Phe Ala Gln Gly
                245                 250

<210> SEQ ID NO 10
<211> LENGTH: 266
<212> TYPE: PRT
<213> ORGANISM: Hordeum vulgare

<400> SEQUENCE: 10

Met Arg Ser Leu Ala Val Val Ala Val Ala Thr Val Ala Met
 1               5                  10                  15

Ala Ile Gly Thr Ala Arg Gly Ser Val Ser Ser Ile Val Ser Arg Ala
                20                  25                  30

Gln Phe Asp Arg Met Leu Leu His Arg Asn Asp Gly Ala Cys Gln Ala
            35                  40                  45

Lys Gly Phe Tyr Thr Tyr Asp Ala Phe Val Ala Ala Ala Ala Ala Phe
 50                  55                  60

Pro Gly Phe Gly Thr Thr Gly Ser Ala Asp Ala Gln Lys Arg Glu Val
 65                  70                  75                  80

Ala Ala Phe Leu Ala Gln Thr Ser His Glu Thr Thr Gly Gly Trp Ala
                85                  90                  95

Thr Ala Pro Asp Gly Ala Phe Ala Trp Gly Tyr Cys Phe Lys Gln Glu
            100                 105                 110

Arg Gly Ala Ser Ser Asp Tyr Cys Thr Pro Ser Ala Gln Trp Pro Cys
        115                 120                 125

Ala Pro Gly Lys Arg Tyr Tyr Gly Arg Gly Pro Ile Gln Leu Ser His
130                 135                 140

Asn Tyr Asn Tyr Gly Pro Ala Gly Arg Ala Ile Gly Val Asp Leu Leu
145                 150                 155                 160

Ala Asn Pro Asp Leu Val Ala Thr Asp Ala Thr Val Gly Phe Lys Thr
                165                 170                 175

Ala Ile Trp Phe Trp Met Thr Ala Gln Pro Pro Lys Pro Ser Ser His
            180                 185                 190

Ala Val Ile Ala Gly Gln Trp Ser Pro Ser Gly Ala Asp Arg Ala Ala
        195                 200                 205

Gly Arg Val Pro Gly Phe Gly Val Ile Thr Asn Ile Ile Asn Gly Gly
210                 215                 220

Ile Glu Cys Gly His Gly Gln Asp Ser Arg Val Ala Asp Arg Ile Gly
225                 230                 235                 240

Phe Tyr Lys Arg Tyr Cys Asp Ile Leu Gly Val Gly Tyr Gly Asn Asn
                245                 250                 255

Leu Asp Cys Tyr Ser Gln Arg Pro Phe Ala
            260                 265

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR primer
```

5' of gt10 EcoRI site.

<400> SEQUENCE: 11
agcaagttca gcctggttaa                                                                      20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: PCR primer
      3' of gt10 EcoRI site.

<400> SEQUENCE: 12
ttatgagtta tttcttccag gg                                                                   22

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: PCR primer
      nt 40 to 57 UDA cDNA.

<400> SEQUENCE: 13
tctgccgtag tgatcatg                                                                        18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: PCR primer
      nt 348 to 329 UDA cDNA.

<400> SEQUENCE: 14
agcggtagct gtagaagc                                                                        18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: PCR primer
      nt 495 to 479 UDA cDNA.

<400> SEQUENCE: 15
atggtagctg tagaagc                                                                         17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: PCR primer
      nt 1044 to 1027 UDA cDNA.

<400> SEQUENCE: 16
gtcgcagtac tcttgta                                                                         17

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: UDA
      mutagensis oligonucleotide 1.

```
<400> SEQUENCE: 17
ggtctagtgt cggcatatgc agaggtgcgg aagc                               34

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: UDA
      mutagenesis oligonucleotide 2.

<400> SEQUENCE: 18
gccagtaccg ctgctaacat atgatcggca agctcgtcg                          39

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: UDA
      mutagenesis oligonucleotide 3.

<400> SEQUENCE: 19
tgttgcggcg taaaacatat gctagtcctc cccaag                             36
```